(12) United States Patent
Zon et al.

(10) Patent No.: US 8,361,753 B2
(45) Date of Patent: Jan. 29, 2013

(54) PHOSPHOTRIESTER-MODIFIED OLIGONUCLEOTIDE PRIMERS FOR NUCLEIC ACID AMPLIFICATION

(75) Inventors: Gerald Zon, San Carlos, CA (US); Alexandre Lebedev, San Diego, CA (US)

(73) Assignee: TriLink BioTechnologies, Inc., San Diego, CA (US)

( * ) Notice: Subject to any disclaimer, the term of this patent is extended or adjusted under 35 U.S.C. 154(b) by 896 days.

(21) Appl. No.: 11/750,237

(22) Filed: May 17, 2007

(65) Prior Publication Data

US 2007/0281308 A1 Dec. 6, 2007

Related U.S. Application Data

(60) Provisional application No. 60/810,665, filed on Jun. 1, 2006.

(51) Int. Cl.
C12P 19/34 (2006.01)
C12Q 1/68 (2006.01)

(52) U.S. Cl. ........................................ 435/91.1; 435/6.1

(58) Field of Classification Search ................... 435/6.1, 435/91.1
See application file for complete search history.

(56) References Cited

U.S. PATENT DOCUMENTS

| 4,683,195 A | 7/1987 | Mullis et al. |
|---|---|---|
| 4,683,202 A | 7/1987 | Mullis |
| 5,578,467 A | 11/1996 | Schuster et al. |
| 5,773,258 A | 6/1998 | Birch et al. |
| 5,830,655 A | 11/1998 | Monforte et al. |
| 5,852,188 A * | 12/1998 | Cook ........................... 536/24.5 |
| 6,001,611 A | 12/1999 | Will |
| 6,057,134 A | 5/2000 | Lader et al. |
| 6,274,353 B1 | 8/2001 | Yang |
| 6,399,304 B1 | 6/2002 | Kilger et al. |
| 6,482,590 B1 | 11/2002 | Ullman et al. |
| 6,762,298 B2 | 7/2004 | Beaucage et al. |
| 2001/0044529 A1 | 11/2001 | Beaucage et al. |
| 2003/0119150 A1 | 6/2003 | Ankenbauer et al. |
| 2003/0162199 A1 | 8/2003 | Bonner |
| 2005/0042644 A1* | 2/2005 | Woo et al. ........................ 435/6 |
| 2007/0009922 A1 | 1/2007 | Borns |

FOREIGN PATENT DOCUMENTS

| EP | 1275735 | 1/2003 |
|---|---|---|
| JP | 2003-038180 | 2/2003 |
| WO | WO-02/18616 | 3/2002 |
| WO | WO 02088387 | 7/2002 |
| WO | WO-2006/005074 | 1/2006 |
| WO | WO-2006/008479 | 1/2006 |
| WO | WO-2007/011901 | 1/2007 |

OTHER PUBLICATIONS

Weinfeld et al., Synthesis and Properties of Oligodeoxyribonucleotides Containing an Ethylated Internucleotide Phosphate, Biochemistry 1986, 25, 5083-5091.*

Miller et al., Synthesis and Template Properties of an Ethyl Phosphotriester Modified Decadeoxyribonucleotide, Biochemistry 1982, 21, 5468-5474.*

(Continued)

Primary Examiner — Jezia Riley
(74) Attorney, Agent, or Firm — Kilpatrick Townsend & Stockton LLP

(57) ABSTRACT

The present invention provides methods and compositions for nucleic acid amplification. These methods involve the use of oligonucleotide primers in temperature dependent nucleic acid amplification reactions. In certain aspects, the methods are accomplished by use of certain modified oligonucleotide primers which provide utility in nucleic acid amplification. In preferred embodiments, the oligonucleotide primers are modified with particular chemical groups such as esters.

34 Claims, 2 Drawing Sheets

OTHER PUBLICATIONS

Cieślak et al, Thermolytic Properties of 3-(2-Pyridyl)-1-propyl and 2-[N-Methyl-N-(2-pyridyl)]aminoethyl Phosphate/Thiophosphate Protecting Groups in Solid-Phase Synthesis of Oligodeoxyribonucleotide, J. Org. Chem. 2003, 68, 10123-10129.*

Ailenberg, M., et al., Controlled Hot Start and Improved Spedificity in Carrying Out PCR Utilizing Touch-Up and Loop Incorporated Primers (TULIPS) BioTechniques, 29(5) 1018-23 (2000).

Barone et al., In situ activation of bis-dialkylaminophosphines—a new method for synthesizing deoxyoligonucleotides on polymer supports, Nucleic Acids Research, 12:4051 (1984).

Budowle, B., et al., Building Microbial Forensics as a Response to Bioterrorism, Science, 301:1852-53 (2003).

Bustin, S.A., et al., Pitfalls of Quantitative Real-Time Reverse-Transcription Polymerase Chain Reaction, J. of Biomolecular Techniques, 15:155-66 (2004).

Cieślak, J., et al., Thermolytic Properties of 3-(2-Pyridyl)-1-propyl and 2-[$N$-Methyl-$N$-(2-pyridyl)]aminoethyl Phosphate/Thiophosphate Protecting Groups in Solid-Phase Synthesis of Oligodeoxyribonucleotides, J. Org. Chem., 68:10123-29 (2003).

Cieślak, J., et al., Thermolytic 4-Methylthio-1-butyl Group for Phosphate/Thiophosphate Protection in Solid-Phase Synthesis of DNA Oligonucleotides, J. Org. Chem., 69:2509-15 (2004).

Dahiya, R., et al., A novel p53 mutation hotspot at codon 132 (AAG→AGG) in human renal cancer. Biochemistry and Molecular Biology International, 44:407-15 (1998).

Deng, C., et al., Oligonucleotide Inhibitors of *Taq* DNA Polymerase Facilitate Detection of Low Copy Number Targets by PCR, J. Mol. Biol., 264:268-78 (1996).

Eastlund, E., et al., Hot Start RT-PCR Results in Improved Performance of the Enhanced Avian RT-PCR System, LifeScience Quarterly, 2:2-5 (2001).

Elnifro, E.M., et al., PCR and Restriction Endonuclease Analysis for Rapid Identification of Human Adenovirus Subgenera, Clin. Microbial. Rev., 13:559-70 (2000).

Gallo, et al., Alkyl phosphotriester modified oligodeoxyribonucleotides. V. Synthesis and absolute configuration of $R_p$ and $S_p$ diastereomers of an ethyl phosphotriester (Et) modified *Eco*RI recognition sequence d[GGAA(Et)TTCC]. A synthetic approach to reglo- and stereospecific ethylation-interference studies, Nucleic Acids Res., 14:7405-7420 (1986).

Grajkowski, et al., The 2-($N$-Formyl-$N$-methyl)aminoethyl Group as a Potential Phosphate/Thiophosphate Protecting Group in Solid-Phase Oligodeoxyribonucleotide Synthesis, Org. Lett., 3:1287-90 (2001).

Hafner, et al., Minimal Circular Template is Required for the Synthesis of Abundant Linear amplimer by *Bst* DNA Polymerase, Biotechniques, 30(4) 852-6, 858, 860 passim (2001).

Kolmodin and Williams, Polymerase chain reaction: Basic principles and routine practice. In *The Nucleic Acid Protocols Handbook*, edited by Ralph Rapley. Totowa, NJ: Humana Press, 569-580 (2000).

Koziolkiewicz et al., P-chiral analogues of oligodeoxyribonucleotides: Synthesis, stereochemistry and enzyme studies. 26 Chem. Scripta, 251-60 (1986).

LaPlanche, et al., Phosphorothioate-modified oligodeoxyribonucleotides. III. NMR and UV spectroscopic studies of the $R_p$—$R_p$, $S_p$—$S_p$, duplexes, [d(GG$_S$AATTCC)]$_2$, derived from diastereomeric O-ethyl phosphorothioates, Nucleic Acids Res., 14:9081-93 (1986).

Lekanne Deprez, R.H., et al., Sensitivity and accuracy of quantitative real-time polymerase chain reaction using SYBR green I depends on cDNA synthesis conditions, Analytical Biochem., 307:63-69 (2002).

Markoulatos, P., et al., Multiplex Polymerase Chain Reaction: A Practical Approach, J. of Clin. Laboratory Analysis, 16:47-51 (2002).

Miller, et al., Synthesis and Properties of Adenine and Thymine Nucleoside Alkyl Phosphotriesters, the Neurtal Analogs of Dinucleoside Monophosphates, J. Am. Chemical Society, 93(24) 6657-65 (1971).

Mizuguchi, H., et al., Characterization and Application to Hot Start PCR of Neutralizing Monoclonal Antibodies against KOD DNA Polymerase, J. Biochem (Tokyo), 126:762-68 (1999).

Moretti, T., et al., Enhancement of PCR Amplification Yield and Specificity Using AmpliTaq™ Gold DNA Polymerase, BioTechniques, 25:716-722 (1998).

Narang, et al., Improved Phosphotriester Method for the Synthesis of Gene Fragments, Meth. Enzymol. 68-90 (1979).

Puskas, L.G., and Bottka, S., Reduction of Mispriming in Amplification Reactions with Restricted PCR, Genome Research, 5:309-311 (1995).

Randall, S.K. et al., Nucleotide Insertion Kinetics Opposite Abasic Lesions in DNA, J. Biological Chemistry, 262:6864-70 (1987).

Saldanha, J., and Minor, P., A Sensitive PCR Method for Detecting HCV RNA in Plasma Pools, Blood Products, and Single Donations, 43 J. Medical Virol., 72-76 (1994).

Sato, et al., HLA typing of aortic tissues from unidentified bodies using hot start polymerase chain reaction-sequence specific primers, Legal Medicine, 5:S91-S193 (2003).

Sauer, et al., Facile method for automated genotyping of single nucleotide polymorphisms by mass spectromerty, Nucleic Acids Res., 30:e22 (2002).

Stec, et al., Synthesis and Absolute Configuration of P-Chiral O-Isopropyl Oligonucleotide Triesters, Tetrahedron Lett., 26:2191-2194 (1985).

Tanzer, et al., A Hot-Start Reverse Transcription-Polymerse Chain Reaction Protocol That Initiates Multiple Analyses Simultaneously, Anal. Biochem., 273:307-310 (1999).

Waldner et al., Hydrophobic Effects in Du;lexes with Modified Oligonucleotide Backbones and RNA, Bioorg. Med. Chem. Letters, 6:2363-66 (1996).

Wharam, et al., Specific detection of DNA and RNA targets using a novel isothermal nucleic acid amplification assay based on the formation of a three-way junction structure, Nucleic Acids Res, 29(11):E54-E54 (2001).

Wilk, A., et al., The 4-oxopentyl group as a labile phosphate/thiophosphate protecting group for synthetic oligodeoxyribonucleotides, Tetrahedron Lett., 42:5635-39 (2001).

Wilk, A., et al., The 3-($N$-*tert*-Butylcarboxamido)-1-propyl Group as an Attractive Phosphate/Thiophosphate Protecting Group for Solid-Phase Oligodeoxyribonucleotide Synthesis, J. Org. Chem., 67:6430-38 (2002).

Zhang, J. and Byrne, C.D., Differential priming of RNA templates during cDNA synthesis markedly affects both accuracy and reproducibility of quantitative competitive reverse-transcriptase PCR, Biochem. J., 337:231-41 (1999).

Zon, Gerald, Synthesis of Backbone-Modified DNA Analogues for Biological Applications, Protein J., 6(2):131-45 (1987).

Chen, et al; Simultaneous genotyping of human platelet antigens by hot start sequence-specified polymerase chain reaction with DNA polymerase AmpliTaq Gold; Vox Sanguinis; (1997); 72(3):192-196.

Communication pursuant to Article 94(3) EPC dated May 6, 2010 in related application EP 0777161.6.

Eggering et al, A one-step coupled amplification and oligonucleotide ligation procedure for multiplex genetic typing, (1995), Genome Res, 4:337-345.

International Search Report dated Sep. 24, 20707 in related application PCT/US2007/011950.

Lebedev, et al: Hot start PCR with heat-activatable primers: a novel approach for improved PCR performance; Nucleic Acids Research; (2008); 36(20):e131.

Levine et al., *E. coli* DNA polymerase. A study on the mechanism of primer binding using oligothymidylate derivatives with ethylated internucleotide phosphate groups. p. 358-369, 1985. (Article is in Russian but an English abstract appears on p. 369), Only Abstract considered.

Murali, Structural studies on an inhibitory antibody against *Thermus aquaticus* DNA polymerase suggest mode of inhibition, Protien Engineering, 1998, 11(2): 79-86.

Nevinsky et al., Procaryotic and eukaryotic DNA polymerases. I. The role of internucleotide phosphates in the binding process of oligonucleotide primer with the enzyme. p. 45-57, 1987. (Article is in Russian but an English abstract appears on p. 57), Only Abstract considered.

Search Report dated Nov. 19, 2009 in related European application EP 07777161.6.

* cited by examiner

PHOSPHOTRIESTER-MODIFIED OLIGONUCLEOTIDE PRIMERS FOR NUCLEIC ACID AMPLIFICATION

CROSS-REFERENCE TO RELATED APPLICATIONS

The present application claims priority to U.S. Provisional Patent Application No. 60/810,665, titled Chemically Modified Oligonucleotide Primers For Nucleic Acid Amplification, filed Jun. 1, 2006, which is incorporated herein by reference.

STATEMENT OF GOVERNMENT SUPPORT

The United States Government has certain rights in this invention pursuant to Grant No. GM072177 awarded by the National Institute for General Medical Science.

FIELD OF THE INVENTION

The present invention relates to methods and compositions for amplifying nucleic acids. In particular aspects, the invention provides methods and compositions for hot start nucleic acid amplification.

BACKGROUND OF THE INVENTION

The following description is provided to assist the understanding of the reader. None of the information provided or references cited is admitted to be prior art in the present invention.

PCR is likely the most widely used method in modern molecular biology and biotechnology, and is rapidly being applied to genetic testing, diagnostics, forensics and biodefense. Kolmodin, L. A., et al., Nucleic Acid Protocols, 569-580 (2000); Budowle, B., et al., 301 Science, 1852-53 (2003); Y. Sato, et al., 5 (Suppl. 1) Legal Medicine, S191-S193 (2003); Saldanha, J., et al., 43 J. Medical Virol., 72-76 (1994); Dahiya, R., et al., 44 Biochemistry and Molecular Biology International, 407-15 (1998); and Elnifro, E. M., et al., 13 Clin. Microbiol. Rev., 559-70 (2000). PCR is described in U.S. Pat. Nos. 4,683,195 and 4,683,202. In each cycle of the PCR amplification process there are typically several steps. The double-stranded DNA target sequence is first thermally denatured at elevated temperatures (~95° C.). The first occurrence of denaturation is referred to herein as the "initial denaturation step." This is followed by annealing of a synthetic oligonucleotide primer to each strand at lower temperatures (~60° C.). These forward and reverse oriented oligonucleotide primers are then each extended from their 3' termini at an elevated temperature (~70° C.) by a thermally stable, magnesium ion-dependent, DNA polymerase which incorporates 5'-deoxynucleotide triphosphates (dNTPs) and generates pyrophosphate (PPi), as depicted in the top portion of FIG. 1 for the forward oligonucleotide primer.

The utility of PCR is driven by its ability to rapidly provide target amplifications of ~$10^6$-fold as well as high specificity, which depends in part on the specificity of oligonucleotide primer hybridization. Oligonucleotide primer sequences and length are therefore designed to hybridize to only the intended target sequence, at the temperatures used for annealing. However, PCR amplification reactions are typically prepared over a period of minutes or hours at ambient room temperatures which are well below the temperature range needed to ensure the specificity of oligonucleotide primer hybridization. Under such less stringent sample preparation conditions, the oligonucleotide primers may bind non-specifically to other sequences having substantial non-complementarity and potentially initiate the synthesis of undesired extension products, which can be amplified along with the target sequence. As has been discussed by Chou, Q., et al., amplification of non-specific sequences by this "mis-priming" can compete with amplification of the desired target sequences, and can therefore significantly decrease the efficiency of the amplification of the desired sequence, especially for low-copy number targets. Chou, Q., et al., 20 Nucleic Acids Res., 1717-23 (1992).

Formation of a "primer dimer" is another problematic form of non-specific hybridization, which, according to Chou, Q., et al., results from amplified extension of two oligonucleotide primers across one another's sequence without significant intervening sequence. These investigations further noted that primer dimers may undergo amplified oligomerization during PCR to create a complex mixture of oligonucleotide primer artifacts, the quality of which often varies inversely with the yield of specific PCR product in low copy number amplifications.

While the aforementioned problems due to mis-priming and primer dimer formation can be encountered in all applications of PCR, these issues can be particularly challenging for high-sensitivity analytical PCR schemes, such as those used for detection of blood-borne infectious agents (Saldanha, J., et al. and Elnifro, E. M., et al.), biohazardous microbes (Budowle, B., et al.) defective or cancerous genes (Dahiya, R., et al), and forensics (Budowle, B., et al. and Y. Sato, et al.). In addition, there is a much greater chance for formation of spurious amplification products in multiplex PCR. Markoulatos, P., et al., 16 J. of Clin. Laboratory Analysis, 47-51 (2002). In reverse transcriptase PCR (RT-PCR), the most sensitive means for detection of a target RNA sequence is to use a gene-specific oligonucleotide primer in the RT step. Zhang, J., et al., 337 Biochem. J., 231-41 (1999); Lekanne Deprez, R. H., et al., 307 Analytical Biochem., 63-69 (2002); and Bustin, S. A., et al., 15 J. of Biomolecular Techniques, 155-66 (2004). In view of the importance of these high-sensitivity applications requiring high specificity to avoid serious, adverse consequences of "false negatives" and "false positives", it is critical to have reagents and protocols which provide assays that are functionally free of artifacts due to mis-priming and primer dimer formation.

A number of general strategies have been investigated for reducing non-specific PCR amplification based on the so-called "hot start" process which aims at impairing undesired amplification due to mis-priming and oligonucleotide primer dimer formation under low-stringency conditions at room temperature during sample preparation. PCR amplification subsequently begins when the amplification reaction mixture reaches high-stringency, "hot" temperatures to "start" polymerase-mediated extension of oligonucleotide primers hybridized only to target sequences. Thus temperature is used to trigger enzymatic extension of the oligonucleotide primers only at elevated temperatures when the stringency of primer/target hybridization conditions are optimal for specificity.

These general strategies for "hot start" include the use of (1) temperature-sensitive materials, such as waxes as barriers or sequestrants to control mixing of the reagents (Q. Chou, et al, and Tanzer, L. R., et al., 273 Anal. Biochem., 307-310 (1999)); (2) oligonucleotide aptamers (Dang, C., et al., 264 J. Mol. Biol., 268-78 (1996)) or antibodies (Eastlund, E., et al., 2 LifeScience Quarterly, 2-5 (2001) and Mizuguchi, H., et al., 126 J. Biochem (Tokyo), 762-68 (1999)) that inhibit the function of DNA polymerases; (3) use of a second thermostable enzyme, such as pyrophosphatase (Clark, D. R., et al., International Patent Application No. WO 2002088387) to remove suppression by added pyrophosphate (PPi); (4) chemically modified polymerases with hydrolytically reversible reagents, such as citraconic acid-modified lysine (Birch, D. E., et al., U.S. Pat. No. 5,773,258) in AmpliTaq Gold (Moretti, T., et al., 25 BioTechniques, 716-722 (1998) and Saldanha, J., et al.) and (5) oligonucleotide primer sequence constructs that disfavor low-temperature mis-priming, such as competitor sequences (Puskas, L. G., et al, 5 Genome Research, 309-311 (1995) or "touch-up and loop-incorporated oligonucleotide primers" (TULIPS-PCR) (Ailenberg, M., et al., 29(5) Bio-Techniques, 1018-23 (2000)).

SUMMARY OF THE INVENTION

The present invention provides methods and compositions for nucleic acid amplification. These methods involve the use of oligonucleotide primers and nucleosides in temperature dependent nucleic acid amplification reactions. In certain aspects, the methods are accomplished by use of certain modified oligonucleotide primers which provide utility in nucleic acid amplification. In preferred embodiments, the oligonucleotide primers are modified with particular chemical groups such as esters.

In one aspect, the invention provides a method of amplifying nucleic acids, the method including amplifying nucleic acid using a modified oligonucleotide primer, where the modified oligonucleotide primer includes one or more modification groups. The modification group dissociates during the initial denaturation step of the amplification. In one embodiment, the modification group includes one or more of the following chemical groups of Formula I, Formula Ia, Formula Ib, Formula Ic, Formula Id, Formula II, Formula III and/or Formula IV as further described herein.

In particular embodiments, the modification group is attached creating a phosphotriester (PTE) internucleotide linkage. The modification impairs DNA polymerase mediated oligonucleotide primer extension prior to the initial incubation period at an elevated temperature of amplification such as in PCR. Oligonucleotide primers made of nucleotides and nucleosides of the present invention have two states. First, the oligonucleotide primer is in an inactive state due to the presence of a modification group until the initial denaturation temperature is reached, often 95° C. Upon reaching the initial denaturation temperature, the oligonucleotide primer becomes active by thermally induced intra molecular fragmentation which converts the oligonucleotide to the second state. This second state of the oligonucleotide primer is the corresponding unmodified oligonucleotide primer which has an active state phosphodiester bond and is extendable by polymerase. Partial or complete dissociation of the modification group preferably occurs after incubation at approximately 95° C. for approximately 2-10 minutes. In certain embodiments, dissociation of the modification group from the oligonucleotide primer occurs in respect to temperature and does not require enzymes, chemicals, or amplification reaction conditions such as pH. Phosphotriester linkages are described in Miller, et al., 93(24) J. Am. Chemical Society, 6657-65 (1971); Zon, et al., 6(2) Protein J., 131-45 (1987); and Koziolkiewicz, M. and Wilk, A., Protocols for Oligonucleotides and Analogs (1993).

In a preferred embodiment, at least one primer of each primer pair in the amplification reaction is labeled with a detectable label. Thus, following amplification, the target segment can be identified by size, affinity capture or color. The detectable label is preferably a fluorescent dye. In some embodiments, different pairs of primers in a multiplex PCR may be labeled with different distinguishable detectable labels. In other embodiments, the forward primer will be labeled with one detectable label, while the reverse primer will be labeled with a different detectable label. Use of different detectable labels is useful for discriminating between amplified products which are of the same length or are very similar in length. Thus, in a preferred embodiment, at least two different fluorescent dyes are used to label different primers used in a single amplification.

In one embodiment, modification groups in accordance with the invention includes compounds of Formula I:

wherein:
L is a straight or branched optionally substituted hydrocarbylene group having between
1-10 carbon atoms, preferably from 2-5 carbon atoms, more preferably from 3-4 carbon atoms, even more preferably 4 carbon atoms;
X is O, S, S(O), S(O)$_2$, C(O), C(S) or C(O)NH; and
R$^1$ is hydrogen or a straight or branched optionally substituted hydrocarbyl group having from 1-20 carbon atoms, preferably 1-10 carbon atoms, more preferably 16 carbon atoms; preferably, the hydrocarbyl is alkyl, alkenyl or alkynyl which may optionally include at least one substituent selected from the group consisting of halo, oxo, hydroxyl, alkoxy, amino, amido, cycloalkyl, heterocycloalkyl, aryl, aryloxy, and heteroaryl.

In one embodiment, modification groups in accordance with the invention provides compounds of Formula Ia:

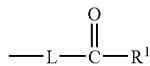

wherein:
L is a straight or branched optionally substituted hydrocarbylene group having between
1-10 carbon atoms, preferably from 2-5 carbon atoms, more preferably from 3-4 carbon atoms, even more preferably 4 carbon atoms; and
R$^1$ is hydrogen or a straight or branched optionally substituted hydrocarbyl group having from 1-20 carbon atoms, preferably 1-10 carbon atoms, more preferably 1-6 carbon atoms; preferably, the hydrocarbyl is alkyl, alkenyl or alkynyl which may optionally include at least one substituent selected from the group consisting of halo, oxo, hydroxyl, alkoxy, amino, amido, cycloalkyl, heterocycloalkyl, aryl, aryloxy, and heteroaryl.

Preferred embodiments of the modification group of Formula Ia are as follows:

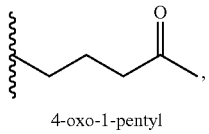

4-oxo-1-pentyl

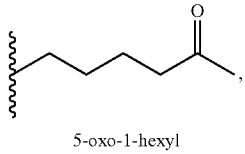

5-oxo-1-hexyl

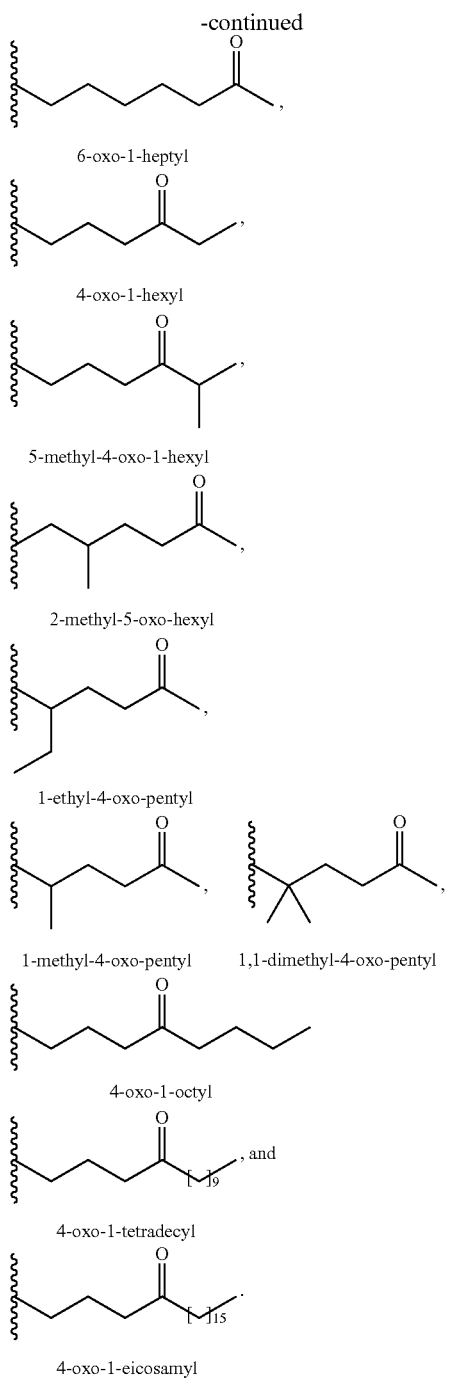

6-oxo-1-heptyl 4-oxo-1-hexyl 5-methyl-4-oxo-1-hexyl 2-methyl-5-oxo-hexyl 1-ethyl-4-oxo-pentyl 1-methyl-4-oxo-pentyl    1,1-dimethyl-4-oxo-pentyl 4-oxo-1-octyl 4-oxo-1-tetradecyl 4-oxo-1-eicosamyl In one embodiment, modification groups in accordance with the invention provide compounds of Formula Ib:

-L-S(O)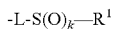—R¹ wherein:
k is an integer from 0-2;
L is a straight or branched optionally substituted hydrocarbylene group having between
1-10 carbon atoms, preferably from 2-5 carbon atoms, more preferably from 3-4 carbon atoms, even more preferably 4 carbon atoms; and
R¹ is hydrogen or a straight or branched optionally substituted hydrocarbyl group
having from 1-20 carbon atoms, preferably 1-10 carbon atoms, more preferably 1-6 carbon atoms; preferably, the hydrocarbyl is alky, alkenyl or alkynyl which may optionally include at least one substituent selected from the group consisting of halo, oxo, hydroxyl, alkoxy, amino, amido, cycloalkyl, heterocycloalkyl, aryl, aryloxy, and heteroaryl.

In a preferred embodiment, the modification group of Formula Ib is 4-methylthio-1-butyl, shown below:

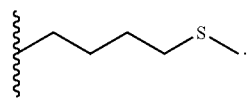 [SMILES: *CCCCSC]

In one embodiment, modification groups in accordance with the invention provide compounds of Formula Ic:

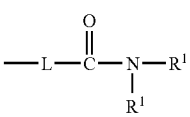

wherein:
L is a straight or branched optionally substituted hydrocarbylene group having between
1-10 carbon atoms, preferably from 2-5 carbon atoms, more preferably from 3-4 carbon atoms, even more preferably 4 carbon atoms; and
R¹ is hydrogen or a straight or branched optionally substituted hydrocarbyl group
having from 1-20 carbon atoms, preferably 1-10 carbon atoms, more preferably 1-6 carbon atoms; preferably, the hydrocarbyl is alkyl, alkenyl or alkynyl which may optionally include at least one substituent selected from the group consisting of halo, oxo, hydroxyl, alkoxy, amino, amido, cycloalkyl, heterocycloalkyl, aryl, aryloxy, and heteroaryl.

In a preferred embodiment, the modification group of Formula Ic is 3-(N-tert-butylcarboxamido)-1-propyl, shown below:

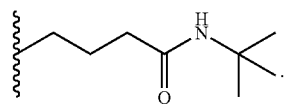 [SMILES: *CCCC(=O)NC(C)(C)C]

In one embodiment, modification groups in accordance with the invention provide compounds of Formula Id:

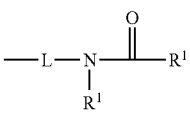

wherein:
L is a straight or branched hydrocarbylene group having between 1-10 carbon atoms,
preferably from 2-5 carbon atoms, more preferably from 3-4 carbon atoms, even more preferably 4 carbon atoms; and Each $R^1$ is independently hydrogen or a straight or branched optionally substituted hydrocarbyl group having from 1-20 carbon atoms, preferably 1-10 carbon atoms, more preferably 1-6 carbon atoms. Preferably the hydrocarbyl is an alkyl, alkenyl or alkynyl which may optionally include at least one substituent selected from the group consisting of halo, oxo, hydroxyl, alkoxy, amino, amido, cycloalkyl, heterocycloalkyl, aryl, aryloxy, and heteroaryl.

Preferred embodiments of the modification group Formula Id include 2-(N-formyl-N-methyl)aminoethyl or 2-(N-acetyl-N-methyl)aminoethyl (shown below):

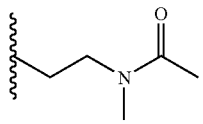 [SMILES: *CCN(C)C(C)=O]

2-(N-acetyl-N-methyl) aminoethyl

In another embodiment, modification groups in accordance with the invention provide compounds of Formula II:

-L-R² wherein:
L is a straight or branched hydrocarbylene group having between 1-10 carbon atoms, preferably from 2-5 carbon atoms, more preferably from 3-4 carbon atoms, even more preferably 4 carbon atoms; and
$R^2$ is hydrogen, cyano, or an optionally substituted carbocycle, heterocycle, aryl or heteroaryl having between 5 and 10 atoms.

In a preferred embodiment, the modification group of Formula II is N-(2-hydroxyethyl)-phthalimido, shown below:

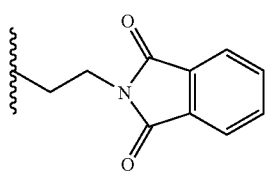 [SMILES: *CCN1C(=O)c2ccccc2C1=O]

N-(2-hydroxyethyl)-phthalimido

In another embodiment, modification groups in accordance with the invention provide compounds of Formula III:

-$L^a$-A-$L^b$-B wherein:
$L^a$ and $L^b$ are each independently selected from a bond or a straight or branched optionally substituted hydrocarbylene group having between 1-8 carbon atoms, preferably from 2-5 carbon atoms, more preferably from 3-4 carbon atoms;
A is O, S, S(O), S(O)$_2$, Se, CR$^3$R$^4$, NR$^3$, C(O), C(S) or CNR$^3$;
B is C(O)R$^3$, C(S)R$^3$, C(O)NR$^3$R$^4$, OR$^3$ or SR$^3$; and
$R^3$ and $R^4$ are each independently hydrogen or straight or branched optionally substituted hydrocarbyl group having from 1-20 carbon atoms, preferably 1-10 carbon atoms, preferably 1-6 carbon atoms; preferably, the hydrocarbyl is alkyl, alkenyl or alkynyl which may optionally include at least one substituent selected from the group consisting of halo, oxo, hydroxyl, alkoxy, amino, amido, cycloalkyl, heterocycloalkyl, aryl, aryloxy, and heteroaryl.

In another embodiment, modification groups in accordance with the invention provide compounds of Formula IV:

-$L^a$-D-$L^b$-E-$L^c$-F wherein:
$L^a$, $L^b$ and $L^c$ are each independently selected from a bond or a straight or branched optionally substituted hydrocarbylene group having between 1-8 carbon atoms, preferably from 2-5 carbon atoms, more preferably from 3-4 carbon atoms;
D is O, S, S(O), S(O)$_2$, CR$^5$R$^6$, or NR$^5$;
E is O, S, S(O), S(O)$_2$, CR$^5$R$^6$, or NR$^6$;
F is hydrogen, C(O)R$^7$, C(S)R$^7$, C(O)NR$^7$R$^8$, OR$^7$ or SR$^7$;
$R^5$ and $R^6$ can each independently be hydrogen, aryl, alkyl, halo, oxo, hydroxyl, alkoxy, aryloxy, or amino, or $R^5$ and $R^6$ can cooperate to form a mono or bicyclic ring consisting 5-10 atoms and including D, $R^5$, $R^6$, E and $L^b$, provided that when $R^5$ and $R^6$ cooperate to form a ring, n is from 0-2; and
$R^7$ and $R^8$ are each independently selected from aryl, alkyl, halo, oxo, hydroxyl, alkoxy, aryloxy, amino, amido, optionally substituted cycloalkyl, optionally substituted hetercycloalkyl, optionally substituted aryl, optionally substituted aryloxy, or optionally substituted heteroaryl.

In one embodiment of a compound of Formula IV wherein $R^5$ and $R^6$ cooperate to form a ring the modification group is methoxymethyl-cyclohex-1,3-yl-ethyl, shown below:

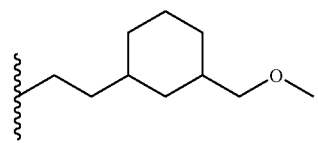 [SMILES: *CCC1CCCC(COC)C1]

methoxymethyl-cyclohex-1,3-yl-ethyl.

In one embodiment, the oligonucleotide primer has a modified backbone of Structure I:

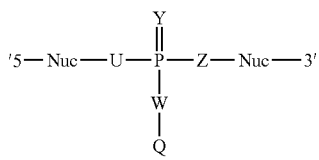

wherein:
Nuc is a nucleoside within the primer sequence
U and Z are independently O, S, Se, NR$^9$, or CR$^9$R$^{10}$;
$R^9$ and $R^{10}$ are each independently hydrogen or straight or branched optionally substituted hydrocarbyl having from 1-10 carbon atoms; preferably, the hydrocarbyl is alkyl, alkenyl or alkynyl wherein each may independently include at least one substituent selected from halo, oxo, hydroxyl, alkoxy, aryloxy, amino, amido or a detectable label;

Y is O, S or Se;

W is any chemical moiety which allows Q to be thermally cleaved, for example, O, S, S(O), S(O)$_2$, Se, C(O), C(S), C(O)NH, C(N)H, NH, —C(=NR$^{11}$)— or NR$^9$;

R$^{11}$ is hydrogen or optionally substituted hydrocarbyl having 1-10 carbon atoms, preferably 1-6 carbon atoms; preferably, R$^{11}$ is H, alkyl or lower alkyl; and Q is a modification group comprising one or more thermally cleavable groups.

In one embodiment, the modification group, Q, includes one or more thermally cleavable groups selected from Formulas I, Ia, Ib, Ic, Id, II, III or IV as defined herein.

In another aspect, the present invention provides for an oligonucleotide primer for nucleic acid amplification including a nucleic acid sequence where the nucleic acid sequence has one or more modification groups. The modification group includes one or more of the following chemical groups of Formula I, Formula Ia, Formula Ib, Formula Ic, Formula Id, Formula II, Formula III and/or Formula IV as further described herein.

In yet another aspect, the present invention provides for a method of manufacturing modified oligonucleotide primers and modified nucleotides for nucleic acid including performing oligonucleotide synthesis with modified phosphoramidites where the modified phosphoramidites comprise one or more of the following modification groups of Formula I, Formula Ia, Formula Ib, Formula Ic, Formula Id, Formula II, Formula III and/or Formula IV as further described herein.

Kits comprising modified oligonucleotides for performing amplifications as described herein are also provided. The kit may include a container marked for nucleic acid amplification, instructions for performing nucleic acid amplification and/or one or more reagents selected from the group consisting of dNTPs, nucleic acid polymerase, magnesium, and reaction buffer.

The methods and compositions of the present invention for nucleic acid amplification are useful in applications that employ synthetic oligonucleotide primers and polymerase extension of nucleic acid. The oligonucleotide primers of the present invention can have a single modification site or multiple modification sites.

In accordance with the present invention, it has been found that the modified oligonucleotides of the present invention have significant advantages. For example, the end user can use the same amplification protocols and methods already in use with unmodified oligonucleotide primers. Modified oligonucleotide primers of the present invention are compatible with existing amplification systems and reagents (including hot start PCR), no additional enzymes or reagents are needed and existing oligonucleotide primer synthesis methods can be used to synthesize the modified oligonucleotide primers of the present invention. Other aspects of the invention include commercial products for this technology includes PTE-modified phosphoramidites, PTE-modified solid supports for oligonucleotide synthesis, oligonucleotide primer sets for commonly amplified targets, and custom synthesized oligonucleotide primer sequences. Polymerase based amplification applications which employ oligonucleotide primers requiring fidelity can be used with the modified oligonucleotide primers of the present invention. Amplification applications include but are not limited to polymerase chain reaction (PCR), hot start PCR, reverse transcription PCR (RT-PCR), multiplex PCR, quantitative PCR (Q-PCR), sequencing or other nucleic acid amplification methods known in the art.

In certain embodiments of the methods and compositions provided herein, amplification is by reverse transcriptase (RT). One of ordinary skill in the art is familiar with the conditions needed to perform RT. The denaturation and extension temperatures may vary and depend on the reverse transcriptase enzyme being used. For example, denaturation and extension by reverse transcriptase occurs at about 37-70° C. Modification groups provided herein can be selected for use according to a desired dissociation condition, such as a particular temperature, or particular temperature in conjunction with a particular time frame. For example, modification groups can be used for RT such that the group dissociates at 37-70° C.; preferably 37-60° C.; preferably at about 50° C.; preferably at about 42° C., and preferably at about 37° C. In other embodiments, the modification group dissociate within 0.1-60 minutes; preferably 1-30 minutes; preferably 1-15 minutes; preferably 1-10 minutes; preferably 0.1-5 minutes at the desired temperature.

In other embodiments of the methods and compositions provided herein, amplification can be one or more than one amplification reaction in a single reaction mixture, such as reverse transcriptase polymerase chain reaction (RT-PCR) or other examples, such as those described in U.S. Pat. No. 6,399,304. In certain embodiments, reagents needed for more than one enzymatic reaction may be added and carried out in a single reaction vessel. In such reactions, various combinations of modified and/or unmodified oligonucleotides may be used. For example, modified oligonucleotides could be used for one, one or more, two or more, three or more, five or more, ten or more of the reactions. In one instance, an oligonucleotide with a modification group could be used for reverse transcriptase that dissociates at temperatures ideal for RT, such as 42° C. and another oligonucleotide with a different modification group could be used for PCR that dissociates at temperatures ideal for PCR, such as 95° C. By providing such a combination, the PCR primers do not interfere or substantially interfere with the RT reaction. Alternatively, the RT primers may be unmodified primers and the PCR primers may be modified with a group that dissociates at temperatures ideal for PCR, such as 95° C. In yet further embodiments, the subsequent PCR includes multiplex PCR, real-time PCR, or quantitative PCR.

In certain other embodiments of the methods and compositions provided herein, amplification comprises one or more than one amplification reactions in a single reaction mixture, such as multiplex PCR. Primers used to amplify different target regions may be included in the same reaction. In such reactions, different combinations of modified and/or unmodified primers may be used for each target region. In using different combinations of unmodified and/or modified primers, relative efficiencies of amplification may be controlled by use of different modification groups. For example, a primer for a first target nucleic acid region may have no modification group while a primer for a second target region has a modification group, where the first target region amplifies less efficiently than the second target region under the same conditions. Alternatively, a primer for a first target region could have one modification group and a primer for a second target region could have a different modification group, where the modification groups have different rates of dissociation. In another alternative, in order to control efficiency of amplification, a mixed population of a modified primer and its unmodified equivalent may be used. In yet further preferred embodiments, the multiplex PCR reaction amplifies two or more, three or more, four or more, five or more, ten or more, or twenty or more different target regions. Any combination of unmodified and modified primers can be used for each target region, preferably one, two, two or more, three or more, five or more, ten or more, or twenty or more different target regions. For example when amplifying three target regions, a first target region may use unmodified primers and the second and third target region may use modified primers, where the primers for the second and third target regions may use the same or different modification groups, and where a primer of one nucleotide sequence (i.e., the forward primer for a first target region) can also be a mixture of modified primers and their unmodified primer equivalent. One of skill in the art would be able to determine what combination of primers and modification groups would be appropriate depending on factors such as dissociation efficiencies of a modification group, amplification efficiency and the number of target regions.

As used herein, the term "amplification" or "amplify" refers to one or more methods known in the art for copying a target nucleic acid, thereby increasing the number of copies of a selected nucleic acid sequence. Amplification of the present invention employs synthetic oligonucleotide primers with nucleic acid polymerase extension including reverse transcriptase (RT). Amplification may be exponential or linear. A target nucleic acid may be DNA, RNA, cDNA or a modified nucleic acid template. While the exemplary methods described hereinafter relate to amplification using the polymerase chain reaction ("PCR"), numerous other methods are known in the art for amplification of nucleic acids. For example methods include isothermal methods, rolling circle methods, real-time PCR, quantitative PCR, multiplex PCR, DNA sequencing and other nucleic acid extension reactions. The skilled artisan will understand that other methods may be used either in place of, or together with, PCR methods. See, e.g. Saiki, "Amplification of Genomic DNA" in PCR Protocols, Innis et al., eds., Academic Press, San Diego, Calif., 13-20 (1990); Wharam, et al., 29(11) Nucleic Acids Res, E54-E54 (2001); Hafner, et al., 30(4) Biotechniques, 852-6, 858, 860 passim (2001); and Zhong, et al., 30(4) Biotechniques, 852-56, 858, 860 passim (2001).

As used herein, "nucleic acid," "nucleotide sequence," or "nucleic acid sequence" refer to nucleotides, oligonucleotide, polynucleotide, or any fragment thereof and to naturally occurring or synthetic molecules. These phrases also refer to DNA or RNA of genomic or synthetic origin which may be single-stranded or double-stranded and may represent the sense or the antisense strand, or to any DNA-like or RNA-like material. An "RNA equivalent," in reference to a DNA sequence, is composed of the same linear sequence of nucleotides as the reference DNA sequence with the exception that all occurrences of the nitrogenous base thymine are replaced with uracil, and the sugar backbone is composed of ribose instead of deoxyribose. Additional alternative nucleic acid backbones suitable for the invention include but are not limited to phosphorothioate, phosphoroselenoate, alkyl phosphonate, aryl phosphonate, Locked Nucleic Acids (LNA), and Peptide Nucleic Acids (PNA) and boronate. RNA may be used in the methods described herein and/or may be converted to cDNA by reverse-transcription for use in the methods described herein.

As used herein, the term "modified oligonucleotide" refers to an oligonucleotide primer having at least one modification group. Modified oligonucleotides include, for example, an oligonucleotide containing a modified nucleoside, an oligonucleotide containing a modified internucleotide linkage, or an oligonucleotide having any combination of modified nucleosides and internucleotide linkages (even if a natural nucleoside is present in the oligonucleotide chain). Oligonucleotides whose nucleosides are connected via modified internucleotide linkages can be found, for example, in Waldner et al., 6 Bioorg. Med. Chem. Letters, 2363-66 (1996), which describes the synthesis of oligonucleotides containing various amide internucleotide linkages.

As used herein, the term "oligonucleotide" "primer" or "oligonucleotide primer" refers to a polynucleotide, usually single stranded, may be naturally occurring or synthetic, usually comprised of a sequence of between about 5 to about 50 nucleotides. more preferably about 10 to about 30 nucleotides or more preferably about 15 to about 25 nucleotides. Oligonucleotides include DNA or RNA. The skilled artisan is capable of designing and preparing primers that are appropriate for amplifying a target sequence. The length of the primer hybridization sequence of amplification primers for use in the present invention depends on several factors including the nucleotide sequence identity, complementarity and the temperature at which these nucleic acids are hybridized or used during in vitro nucleic acid amplification. The considerations necessary to determine a preferred length for the primer hybridization sequence of an amplification primer of a particular sequence identity are well known to the person of ordinary skill. For example, the length of a short nucleic acid or oligonucleotide can relate to its hybridization specificity or selectivity.

As used herein, the term "modification group" refers to a chemical moiety attached to an oligonucleotide primer. In certain embodiments, the chemical moiety is an ester. An oligonucleotide primer which comprises one or more modification groups of the present invention has reduced efficacy for nucleic acid extension. Preferably, extension is impaired when the inactive state of a modified oligonucleotide primer is at least 50% less efficacious at priming an amplification reaction than its corresponding oligonucleotide in the active state, preferably at least 60% less efficacious, preferably 70% less efficacious, more preferably at least 80% less efficacious, more preferably less than 90% less efficacious and even more preferably 95% less efficacious at priming an amplification reaction than its corresponding oligonucleotide primer in the active state. One of ordinary skill in the art is able to readily determine level of activity and efficacy. There are many ways to examine priming ability known by one of ordinary skill in the art. One method of determining priming efficacy is illustrated in Example 4 Randall, S. K. et al., 262 J. Biological Chemistry, 6864-70 (1987). Preferably, modification groups are heat labile and dissociate from a modified oligonucleotide at an increasing rate as the temperature of the amplification reaction medium is raised. The modification group may be between two adjacent nucleotides.

As used herein, the term "terminus" with respect to oligonucleotide refers to the nucleotides at or near the 3' or 5' end of an oligonucleotide. Preferably the terminus of a nucleotide includes the terminal 6 nucleotides, more preferably the terminal 5 nucleotides, more preferably the terminal 4 nucleotides, more preferably the terminal 3 nucleotides, more preferably the terminal 2 nucleotides, or more preferably the terminal nucleotide.

As used herein, the term "dissociate" or "dissociation" refers to the separation of a modification group from an oligonucleotide. Dissociation may be partial or complete.

As used herein, the term "internucleotide linkage" refers to the bond between two nucleotides of an oligonucleotide primer.

As used herein, the term "target nucleic acid sequence" or "nucleic acid target" refers to a sequence of nucleotides to be identified.

As used herein, "labels" or "detectable labels" refers to any molecule (or combinations of molecules) that may be attached or otherwise associated with a molecule so that the molecule can be detected indirectly by detecting the detectable label. A detectable label can be a radioisotope (e.g., iodine, indium, sulfur, hydrogen etc.) a dye or fluorophore (e.g., cyanine, fluorescein, rhodamine), protein (e.g., avidin, antibody), enzyme (peroxidase, phosphatase, and the like), haptens (e.g., biotin) or any other agent that can be detected directly or indirectly. An enzyme is an example of a detectable label detected by indirect means. In this case, the enzyme is attached to the target nucleic acid and the presence of the enzyme is detected by adding an appropriate substrate that when acted upon by the enzyme, causes the substrate to change in color or to release a cleavage product that provides a different color from the original substrate.

As used herein, the term "heat induction" refers to a process by which the oligonucleotide primer modification is removed from the oligonucleotide primer generating an active state oligonucleotide primer by applying heat thus making it extendable by polymerases.

As used herein, the term "hot start" refers to a nucleic acid amplification reaction wherein polymerase induced nucleic acid amplification is impaired until the reaction reaches an initial temperature above the extension temperature of the enzyme. In hot start PCR applications, initial temperatures reach between about 80-105° C.; or until the amplification reaction reaches an initial temperature of at least about 80° C., or until the amplification reaction reaches an initial temperature of at least about 85° C., or until the amplification reaction an initial temperature of at least about 90° C., or until the amplification reaction reaches an initial temperature of at least about 95° C. The term "hot start" is well known in the art and there are a number of methods known to impair amplification such as modified polymerases, oligonucleotides with secondary structures impairing hybridization and reagents contained in temperature sensitive barriers such as wax. In a preferred embodiment, hot start amplification is caused by heat induced removal of an oligonucleotide modification group.

As used herein, the term "intramolecular fragmentation" refers to the process which the modification group dissociates from a modified oligonucleotide primer. Preferably, the resulting oligonucleotide is in an active state.

As used herein, the term "mis-priming" refers to non-specific oligonucleotide primer binding. In particular the sequences having substantial non-complementarity and potentially initiating synthesis of undesired extension products, which can be amplified along with the target sequence.

As used herein, the term "inactive state" or "inactive" in the context of an oligonucleotide primer, refers to an oligonucleotide primer with a modification group. In one embodiment, the modification group impairs hybridization of the oligonucleotide primer to a target sequence. In another embodiment, the modification group impairs polymerase extension when the oligonucleotide primer hybridizes to another sequence.

As used herein, the term "active state" or "active" in the context of an oligonucleotide primer, refers an oligonucleotide primer without a modification group. Preferably, an active oligonucleotide primer has 1) an unmodified phosphodiester linkage and 2) an unmodified base moiety and is capable of chain extension for use in amplification reactions. An active state oligonucleotide primer may be an oligonucleotide primer that has never had a modification group or an oligonucleotide primer from which a modification group has been removed.

As used herein, the term "primer dimer" refers to non-specific oligonucleotide primer hybridization which results from amplified extension of two oligonucleotide primers across one another's sequence without significant intervening sequence.

As used herein, the term "hybridize" or "specifically hybridize" refers to a process where two complementary nucleic acid strands anneal to each other under appropriately stringent conditions. Hybridizations to target nucleic acids are typically and preferably conducted with probe-length nucleic acid molecules, preferably 20-100 nucleotides in length. Nucleic acid hybridization techniques are well known in the art. See, e.g., Sambrook, et al., Molecular Cloning: A Laboratory Manual, Second Edition, Cold Spring Harbor Press, Plainview, N.Y. (1989); Ausubel, F. M. et al., Current Protocols in Molecular Biology, John Wiley & Sons, Secaucus, N.J. (1994).

As used herein, the term "stringent hybridization condition" refers to hybridization conditions which do not allow for hybridization of two nucleic acids which are not completely complementary.

As used herein, the term "sample" or "test sample" refers to any liquid or solid material believed to comprise nucleic acids of interest. A test sample may be obtained from any biological source (i.e., a biological sample), such as cells in culture or a tissue sample or synthetically produced including a chemically synthesized template.

As used herein, the terms "complement" "complementary" or "complementarity" are used in reference to polynucleotides (i.e., a sequence of nucleotides such as an oligonucleotide or a target nucleic acid) according to standard Watson/Crick pairing rules. A complement sequence can also be a sequence of RNA complementary to the DNA sequence or its complement sequence, and can also be a cDNA. For example, for the sequence "5'-A-G-T-3'" is complementary to the sequence "3'-T-C-A-5'." Certain nucleotides not commonly found in natural nucleic acids may be included in the nucleic acids described herein; these include, modified nucleosides, nucleotides, and nucleic acids, such as inosine, 7-deazaguanine, Locked Nucleic Acids (LNA), and Peptide Nucleic Acids (PNA). Complementarity need not be perfect; stable duplexes may contain mismatched base pairs, degenerative, or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

Complementarity may be "partial" in which only some of the nucleotide bases of two nucleic acid strands are matched according to the base pairing rules. Complementarity may be "complete" or "total" where all of the nucleotide bases of two nucleic acid strands are matched according to the base pairing rules. Complementarity may be absent where none of the nucleotide bases of two nucleic acid strands are matched according to the base pairing rules. The degree of complementarity between nucleic acid strands has significant effects on the efficiency and strength of hybridization between nucleic acid strands. This is of particular importance in amplification reactions, as well as detection methods that depend upon binding between nucleic acids. Either term may also be used in reference to individual nucleotides, especially within the context of polynucleotides For example, a particular nucleotide within an oligonucleotide may be noted for its complementarity, or lack thereof, to a nucleotide within another nucleic acid strand, in contrast or comparison to the complementarity between the rest of the oligonucleotide and the nucleic acid strand.

As used herein, the term "substantially complementary" refers to two sequences that hybridize under stringent hybridization conditions. The skilled artisan will understand that substantially complementary sequences need not hybridize along their entire length. In particular, substantially complementary sequences comprise a contiguous sequence of bases that do not hybridize to a target sequence, positioned 3' or 5' to a contiguous sequence of bases that hybridize under stringent hybridization conditions to a target sequence.

As used herein, the term "forward primer" refers to an oligonucleotide primer that anneals to the anti-sense strand of single stranded RNA, single stranded DNA, or double stranded DNA. A "reverse primer" anneals to the sense strand of single stranded RNA, single stranded DNA, or double stranded DNA.

As used herein, an oligonucleotide primer is "specific" for a nucleic acid if the oligonucleotide primer hybridization sequence of the oligonucleotide primer has at least 50% sequence identity with a portion of the nucleic acid when the oligonucleotide primer and the nucleic acid are aligned. An oligonucleotide primer that is specific for a nucleic acid is one that, under the appropriate hybridization or washing conditions, is capable of hybridizing to the target of interest and not substantially hybridizing to nucleic acids which are not of interest. Higher levels of sequence identity are preferred and include at least 75%, at least 80%, at least 85%, at least 90%, and at least 95% and more preferably at least 98% sequence identity.

As used herein, the term "nucleoside" includes all modified and naturally occurring nucleosides, including all forms of furanosides found in nucleic acids. Naturally occurring nucleosides include, for example, adenosine, guanosine, cytidine, thymidine, and uridine.

As used herein, the terms "nucleoside analogs," "modified nucleosides," or "nucleoside derivatives" include synthetic nucleosides as described herein. Nucleoside derivatives also include nucleosides having modified base moieties, with or without protecting groups. Such analogs include, for example, deoxyinosinine, 2,6-diaminopurine-2'-deoxy riboside, 5-methyl-2'-deoxycytidine, and the like. The base rings most commonly found in naturally occurring nucleosides are purine and pyrimidine rings. Naturally occurring purine rings include, for example, adenine, guanine, and N6-methyladenine. Naturally occurring purine rings include, for example, cytosine, thymine, and 5'-methylcytosine. The compounds and methods of the present invention include such base rings and synthetic analogs thereof, as well as unnatural heterocycle-substituted base sugars, and even acyclic substituted base sugars. Moreover, nucleoside derivatives include other purine and pyrimidine derivatives, for example, halogen-substituted purines (e.g. 6-fluoropurine), halogen-substituted pyrimidines, $N^6$-ethyladenine, N-(alkyl)-cytosines, 5-ethylcytosine, and the like. Nucleoside derivatives and analogs encompass a wide variety of modifications, such as those described in U.S. Pat. No. 6,762,298.

As used herein, the term "acyl" denotes groups —C(O)$R^a$, where $R^a$ is hydrogen, lower alkyl, substituted lower alkyl, aryl, substituted aryl and the like as defined herein.

As used herein, the term "substituted acyl" denotes the group —C(O)$R^a$, where $R^a$ is substituted lower alkyl, substituted aryl, substituted heteroaryl and the like.

As used herein, the term "acyloxy" denotes the group —OC(O)$R^b$, where $R^b$ is hydrogen, lower alkyl, substituted lower alkyl, cycloalkyl, substituted cycloalkyl, heterocyclyl, substituted heterocyclyl, aryl, substituted aryl, heteroaryl, substituted heteroaryl and the like.

As used herein, the term "alkenyl" means a straight-chain or branched-chain hydrocarbyl, which has one or more double bonds and, unless otherwise specified, contains from about 2 to about 20 carbon atoms, preferably from about 2 to about 10 carbon atoms, more preferably from about 2 to about 8 carbon atoms, and most preferably from about 2 to about 6 carbon atoms. Examples of alkenyl radicals include vinyl, allyl, 1,4-butadienyl, isopropenyl, and the like.

As used herein, the term "alkenylaryl" refers to alkenyl-substituted aryl groups and "substituted alkenylaryl" refers to alkenylaryl groups further bearing one or more substituents as set forth herein.

As used herein, the term "alkenylene" refers to divalent straight or branched chain hydrocarbyl groups having at least one carbon-carbon double bond, and typically containing 2-20 carbon atoms, preferably 2-12 carbon atoms, preferably 2-8 carbon atoms, and "substituted alkenylene" refers to alkenylene groups further bearing one or more substituents as set forth herein.

As used herein, the term "alkyl" refers to a chain of single bond carbons usually ranging from 1-20 carbon atoms, preferably 1-8 carbon atoms, examples include methyl, ethyl, propyl, isopropyl, and the like. Examples of such alkyl radicals include methyl, ethyl, propyl, isopropyl, n-butyl, sec-butyl, isobutyl, tert-butyl, pentyl, isoamyl, hexyl, octyl, dodecanyl, and the like.

As used herein, the term "lower alkyl" refers to a straight chain or a branched chain of carbons usually ranging from 1-6 carbon atoms, preferably 2-5 carbon atoms. Examples include ethyl, propyl, isopropyl, and the like.

As used herein, the term "alkylene" refers to a divalent hydrocarbyl containing 1-20, preferably 1-15 carbon atoms, straight chain or branched, from which two hydrogen atoms are taken from the same carbon atom or from different carbon atoms. Examples of alkylene include, but are not limited to, methylene (—CH$_2$—), ethylene (—CH$_2$CH$_2$—), and the like.

As used herein, the term "alkynyl" means a straight-chain or branched-chain hydrocarbyl, which has one or more triple bonds and contains from about 2-20 carbon atoms, preferably from about 2-10 carbon atoms, more preferably from about 2-8 carbon atoms, and most preferably from about 2-6 carbon atoms. Examples of alkynyl radicals include ethynyl, propynyl (propargyl), butynyl, and the like.

As used herein, the term "alkynylaryl" refers to alkynyl-substituted aryl groups and "substituted alkynylaryl" refers to alkynylaryl groups further bearing one or more substituents as set forth herein.

As used herein, the term "alkoxy" denotes the group —O$R^c$, where $R^c$ is lower alkyl, substituted lower alkyl, acyl, aryl, substituted aryl, aralkyl, substituted aralkyl, heteroalkyl, heteroarylalkyl, cycloalkyl, substituted cycloalkyl, cycloheteroalkyl, or substituted cycloheteroalkyl as defined.

As used herein, the term "lower alkoxy" denotes the group —O$R^d$, where $R^d$ is lower alkyl.

As used herein, the term "alkylaryl" refers to alkyl-substituted aryl groups and "substituted alkylaryl" refers to alkylaryl groups further bearing one or more substituents as set forth herein.

As used herein, the term "alkylcarbonylamino" denotes the group —N$R^e$C(O)$R^f$, wherein $R^e$ is optionally substituted alkyl, and $R^f$ is hydrogen or lower alkyl.

As used herein, the term "alkylsulfinyl" denotes the group —S(O)$R^g$ wherein $R^g$ is optionally substituted alkyl.

As used herein, the term "alkylsulfonyl" denotes the group —S(O)$_2R^g$, wherein $R^g$ is optionally substituted alkyl.

As used herein, the term "alkylsulfonylamino" denotes the group —N$R^e$S(O)$_2R^f$, wherein $R^e$ is optionally substituted alkyl, and $R^f$ is hydrogen or lower alkyl.

As used herein, the term "alkylthio" refers to the group —S—$R^h$, where $R^h$ is lower alkyl or alkoxy.

As used herein, the term "substituted alkylthio" refers to the group —S—R$^i$, where R$^i$ is substituted lower alkyl or alkoxy.

As used herein, the term "alkynylene" refers to divalent straight or branched chain hydrocarbyl groups having at least one carbon-carbon triple bond, and typically having in the range of about 2-12 carbon atoms, preferably 2-8 carbon atoms, and "substituted alkynylene" refers to alkynylene groups further bearing one or more substituents as set forth herein.

As used herein, the term "amido" denotes the group —C(O)NR$^j$R$^{j'}$, where R$^j$ and R$^{j'}$ may independently be hydrogen, lower alkyl, substituted lower alkyl, aryl, substituted aryl, heteroaryl, substituted heteroaryl as defined herein.

As used herein, the term "substituted amido" denotes the group —C(O)NR$^k$R$^{k'}$, wherein R$^k$ and R$^{k'}$ are independently hydrogen, lower alkyl, substituted lower alkyl, aryl, substituted aryl, heteroaryl, or substituted heteroaryl, provided, however, that at least one of R$^k$ and R$^{k'}$ is not hydrogen. R$^k$R$^{k'}$ in combination with the nitrogen may form an optionally substituted heterocyclic or heteroaryl ring.

As used herein, the term "amidino" denotes the group —C(=NR$^m$)NR$^{m'}$R$^{m''}$, wherein R$^m$, R$^{m'}$, and R$^{m''}$ are independently hydrogen or optionally substituted lower alkyl.

As used herein, the term "amino" or substituted amine denotes the group —NR$''$R$'''$, where R$''$ and R$'''$ may independently be hydrogen, lower alkyl substituted lower alkyl aryl, substituted aryl, heteroaryl, or substituted heteroaryl as defined herein, acyl or sulfonyl. A "divalent amine" denotes the group —NH—. A "substituted divalent amine" denotes the group —NR— wherein R is lower alkyl, substituted lower alkyl, aryl, substituted aryl, heteroaryl, substituted heteroaryl, acyl, substituted acyl, sulfonyl or substituted sulfonyl.

As used herein, the term "substituted amino" or "substituted amine" denotes the group —NR$^p$R$^{p'}$, wherein R$^p$ and R$^{p'}$ are independently hydrogen, lower alkyl, substituted lower alkyl, aryl, substituted aryl, heteroaryl, substituted heteroaryl, acyl, substituted acyl, sulfonyl or substituted sulfonyl, provided, however, that at least one of R$^p$ and R$^{p'}$ is not hydrogen. R$^p$R$^{p'}$ in combination with the nitrogen may form an optionally substituted heterocyclic or heteroaryl ring.

As used herein, the term "arylalkynyl" refers to aryl-substituted alkynyl groups and "substituted arylalkynyl" refers to arylalkynyl groups further bearing one or more substituents as set forth herein.

As used herein, the term "aralkyl" means alkyl as defined herein, wherein an alkyl hydrogen atom is replaced by an aryl as defined herein. Examples of aralkyl radicals include benzyl, phenethyl, 1-phenylpropyl, 2-phenylpropyl, 3-phenylpropyl, 1-naphthylpropyl, 2-naphthylpropyl, 3-naphthylpropyl, 3-naphthylbutyl, and the like.

As used herein, the term "aroyl" refers to aryl-carbonyl species such as benzoyl and "substituted aroyl" refers to aroyl groups further bearing one or more substituents as set forth herein.

As used herein, the term "arylalkyl" refers to aryl-substituted alkyl groups and "substituted arylalkyl" refers to arylalkyl groups further bearing one or more substituents as set forth herein.

As used herein, the term "aryl" alone or in combination means phenyl or naphthyl optionally carbocyclic fused with a cycloalkyl of preferably 5-7, more preferably 5-6, ring members and/or optionally substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heteroceyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonyl amino, heteroarylcarbonyl amino, or the like.

As used herein, the term "arylcarbonylamino" denotes the group —NR$^q$C(O)R$^r$, wherein R$^q$ is hydrogen or lower alkyl and R$^r$ is optionally substituted aryl.

As used herein, the term "arylene" refers to divalent aromatic groups typically having in the range of 6 up to 14 carbon atoms and "substituted arylene" refers to arylene groups further bearing one or more substituents as set forth herein.

As used herein, the term "aryloxy" denotes the group —OAr, where Ar is an aryl, or substituted aryl, group.

As used herein, the term "arylsulfonylamino" denotes the group —NR$^q$S(O)$_2$R$^r$, wherein R$^q$ is hydrogen or lower alkyl and R$^r$ is optionally substituted aryl.

As used herein, reference to "a carbamate group" embraces substituents of the structure —O—C(O)—NR$_2$, wherein each R is independently H, alkyl, substituted alkyl, aryl or substituted aryl as set forth herein.

As used herein, reference to "a dithiocarbamate group" embraces substituents of the structure —S—C(S)—NR$_2$, wherein each R is independently H, alkyl, substituted alkyl, aryl or substituted aryl as set forth herein.

As used herein the term "carbocycle" means a saturated, unsaturated, or aromatic group having a single ring or multiple condensed rings composed of linked carbon atoms. The ring(s) can optionally be unsubstituted or substituted with, e.g., halogen, lower alkyl, alkoxy, alkylthio, acetylene, amino, amido, carboxyl, hydroxyl, aryl, aryloxy, heterocycle, hetaryl, substituted hetaryl, nitro, cyano, thiol, sulfamido, and the like.

As used herein, the term "cycloalkenyl" refers to cyclic ring-containing groups containing in the range of 3 up to 20 carbon atoms and having at least one carbon-carbon double bond, and "substituted cycloalkenyl" refers to cycloalkenyl groups further bearing one or more substituents as set forth herein.

As used herein, the term "cycloalkyl" refers to a monocyclic or polycyclic alkyl group containing 3 to 15 carbon atoms, and "substituted cycloalkyl" refers to cycloalkyl groups further bearing one or more substituents as set forth herein.

As used herein, the term "cycloalkylene" refers to divalent ring-containing groups containing in the range of about 3 up to about 12 carbon atoms, and "substituted cycloalkylene" refers to cycloalkylene groups further bearing one or more substituents as set forth herein.

As used herein, the term "guanidinyl" refers to the structure —N=C(NH$_2$)$_2$ and "substituted guanidinyl" refers to the structure —N=C(NR$_2$)$_2$, wherein each R is independently H, alkyl, substituted alkyl, aryl or substituted aryl as set forth herein.

As used herein, the term "halo" or "halogen"—alone or in combination means all halogens, that is, chloro (Cl), fluoro (F), bromo (Br), iodo (I).

As used herein, the term "heteroaryl" alone or in combination refers to a monocyclic aromatic ring structure containing 5 or 6 ring atoms, or a bicyclic aromatic group having 8 to 10 atoms, containing one or more, preferably 1-4, more preferably 1-3, even more preferably 1-2, heteroatoms independently selected from the group O, S, and N, and optionally substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable aromatic ring is retained. Examples of heteroaryl groups are phthalimide, pyridinyl, pyridazinyl, pyrazinyl, quinazolinyl, purinyl, indolyl, quinolinyl, pyrimidinyl, pyrrolyl, oxazolyl, thiazolyl, thienyl, isoxazolyl, oxathiadiazolyl, isothiazolyl, tetrazolyl, imidazolyl, triazinyl, furanyl, benzofuryl, indolyl and the like. A substituted heteroaryl contains a substituent attached at an available carbon or nitrogen to produce a stable compound.

As used herein, the term "substituted heteroaryl" refers to a heterocycle optionally mono or poly substituted with one or more functional groups, e.g., halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

As used herein, the term "heteroarylcarbonylamino" denotes the group —NR$^q$C(O)R$^r$, wherein R$^q$ is hydrogen or lower alkyl and R$^r$ is optionally substituted aryl.

As used herein, the term "heteroaryloxy" denotes groups —OHet, wherein Het is an optionally substituted heteroaryl group.

As used herein, the term "heteroarylsulfonylamino" denotes the group —NR$^q$S(O)$_2$R$^s$, wherein R$^q$ is hydrogen or lower alkyl and R$^s$ is optionally substituted heteroaryl.

As used herein, the term "heterocycle" refers to a saturated, unsaturated, or aromatic group having a single ring (e.g., morpholino, pyridyl or furyl) or multiple condensed rings (e.g., naphthpyridyl, quinoxalyl, quinolinyl, indolizinyl or benzo[b]thienyl) and having carbon atoms and at least one hetero atom, such as N, O or S, within the ring, which can optionally be unsubstituted or substituted with, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido and the like.

As used herein, the term "substituted heterocycle" is a heterocycle substituted with 1 or more, e.g., 1, 2, or 3, substituents selected from the group consisting of optionally substituted alkyl, optionally substituted alkenyl, optionally substituted alkynyl, halo, hydroxy, alkoxy, alkylthio, alkylsulfinyl, alkylsulfonyl, acyloxy, aryl, substituted aryl, aryloxy, heteroaryloxy, amino, amido, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, acyl, carboxyl, heterocycle, substituted heterocycle, hetaryl, substituted hetaryl, nitro, cyano, thiol, sulfonamido, and oxo, attached at any available point to produce a stable compound.

As used herein, the term "hydrocarbyl" comprises any organic radical wherein the backbone thereof comprises carbon and hydrogen only. Thus, hydrocarbyl embraces alkyl, cycloalkyl, alkenyl, cycloalkenyl, alkynyl, aryl, alkylaryl, arylalkyl, arylalkenyl, alkenlyaryl, arylalkynyl, alkynylaryl, and the like.

As used herein, the term "substituted hydrocarbyl" comprises any of the above-referenced hydrocarbyl groups further bearing one or more substituents selected from hydroxy, hydrocarbyloxy, substituted hydrocarbyloxy, alkylthio, substituted alkylthio, arylthio, substituted arylthio, amino, alkylamino, substituted alkylamino, carboxy, —C(S)SR, —C(O)SR, —C(S)NR$_2$, wherein each R is independently hydrogen, alkyl or substituted alkyl, nitro, cyano, halo, —SO$_3$M or, —OSO$_3$M, wherein M is H, Na, K, Zn Ca, or meglumine, guanidinyl, substituted guanidinyl, hydrocarbyl, substituted hydrocarbyl, hydrocarbylcarbonyl, substituted hydrocarbylcarbonyl, hydrocarbyloxycarbonyl, substituted hydrocarbyloxycarbonyl, hydrocarbylcarbonyloxy, substituted hydrocarbylcarbonyloxy, acyl, acyloxy, heterocyclic, substituted heterocyclic, heteroaryl, substituted heteroaryl, heteroarylcarbonyl, substituted heteroarylcarbonyl, carbamoyl, monoalkylcarbamoyl, dialkylcarbamoyl, arylcarbamoyl, a carbamate group, a dithiocarbamate group, aroyl, substituted aroyl, organosulfonyl, substituted organosulfonyl, organosulfinyl, substituted alkylsulfinyl, alkylsulfonylamino, substituted alkylsulfonylamino, arylsulfonylamino, substituted arylsulfonylamino, a sulfonamide group, sulfuryl, and the like, including two or more of the above-described groups attached to said hydrocarbyl moiety by such linker/spacer moieties as —O—, —S—, —NR—, wherein R is hydrogen, alkyl or substituted alkyl, —C(O)—, —C(S)—, —C(=NR')—, —C(=CR'$_2$)—, wherein R' is alkyl or substituted alkyl, —O—C(O)—, —O—C(O)—O—, —O—C(O)—NR— (or —NR—C(O)—O—), —NR—C(O)—, —NR—C(O)—NR—, —S—C(O)—, —S—C(O)—O—, —S—C(O)—NR—, —O—S(O)$_2$—, —O—S(O)$_2$—O—, —O—S(O)$_2$—NR—, —O—S(O)—, —O—S(O)—O—, —O—S(O)—NR—, —O—NR—C(O)—, —O—NR—C(O)—O—, —O—NR—C(O)—NR—, —NR—O—C(O)—, —NR—O—C(O)—O—, —NR—O—C(O)—NR—, —O—NR—C(S)—, —O—NR—C(S)—O—, —O—NR—C(S)—NR—, —NR—O—C(S)—, —NR—O—C(S)—O—, —NR—O—C(S)—NR—, —O—C(S)—, —O—C(S)—O—, —O—C(S)—NR— (or —NR—C(S)—O—), —NR—C(S)—, —NR—C(S)—NR—, —S—S(O)$_2$—, —S—S(O)$_2$—O—, —S—S(O)$_2$—NR—, —NR—O—S(O)—, —NR—O—S(O)—O—, —NR—O—S(O)—NR—, —NR—O—S(O)$_2$—, —NR—O—S(O)$_2$—O—, —NR—O—S(O)$_2$—NR—, —O—NR—S(O)—, —O—NR—S(O)—O—, —O—NR—S(O)—NR—, —O—NR—S(O)$_2$—O—, —O—NR—S(O)$_2$—NR—, —O—NR—S(O)$_2$—, —O—P(O)R$_2$—, —S—P(O)R$_2$—, —NR—(O)R$_2$—, wherein each R is independently hydrogen, alkyl or substituted alkyl, and the like.

As used herein, "hydrocarbyloxy" refers to —O—-hydrocarbyl groups containing 2-20 carbon atoms and "substituted hydrocarbyloxy" refers to hydrocarbyloxy groups further bearing one or more substituents as set forth herein.

As used herein, "hydrocarbylcarbonyl" refers to —C(O)-hydrocarbyl groups containing 2-20 carbon atoms and "substituted hydrocarbylcarbonyl" refers to hydrocarbylcarbonyl groups further bearing one or more substituents as set forth herein.

As used herein, "hydrocarbyloxycarbonyl" refers to —C(O)—O-hydrocarbyl containing 2-20 carbon atoms and "substituted hydrocarbyloxycarbonyl" refers to hydrocarbyloxycarbonyl groups further bearing one or more substituents as set forth herein.

As used herein, "hydrocarbylcarbonyloxy" refers to —O—C(O)-hydrocarbyl groups 2-20 carbon atoms and "substituted hydrocarbylcarbonyloxy" refers to hydrocarbylcarbonyloxy groups further bearing one or more substituents as set forth herein.

As used herein, "hydrocarbylene" comprises any divalent organic radical wherein the backbone thereof comprises carbon and hydrogen only. Thus, hydrocarbylene embraces alkylene, cycloalkylene, alkenylene, cycloalkenylene, alkynylene, arylene, alkylarylene, arylalkylene, arylalkenylene, alkenylarylene, arylalkynylene, alkynylarylene, and the like, and "substituted hydrocarbylene" refers to any of the above-referenced hydrocarbylene groups further bearing one or more substituents as set forth herein.

As used herein, the terms "hydroxyl" and "hydroxy" refer to the group —OH.

As used herein, the term "organosulfinyl" refers to substituents having the structure —S(O)-organo, wherein organo embraces alkyl-, alkoxy-, alkylamino-, and aryl moieties, as well as substituted alkyl-, alkoxy-, alkylamino-, and aryl moieties.

As used herein, the term "organosulfonyl" refers to substituents having the structure —S(O)$_2$-organo, wherein organo embraces alkyl-, alkoxy- and alkylamino-moieties, as well as substituted alkyl-, alkoxy- or alkylamino-moieties.

As used herein, the term "oxo" refers to an oxygen substituent double bonded to the attached carbon.

As used herein, the term "sulfinyl" denotes the group —S(O)—.

As used herein, the term "substituted sulfinyl" denotes the group —S(O)R$^t$, where R$^t$ is lower alkyl, substituted lower alkyl, cycloalkyl, substituted cycloalkyl, cycloalkylalkyl, substituted cycloalkylalkyl, heterocyclyl, substituted heterocyclyl, heterocyclylalkyl, substituted hetereocyclylalkyl, aryl, substituted aryl, heteroaryl, substituted heteroaryl, heteroaralkyl substituted heteroaralkyl, aralkyl or substituted aralkyl.

As used herein, the term "sulfonyl" denotes the group —S(O)$_2$—.

As used herein, the term "substituted sulfonyl" denotes the group —S(O)$_2$R$^t$, where R$^t$ is lower alkyl, substituted lower alkyl, cycloalkyl, substituted cycloalkyl, cycloalkylalkyl, substituted cycloalkylalkyl, heterocyclyl, substituted heterocyclyl, heterocyclylalkyl, substituted hetereocyclylalkyl, aryl, substituted aryl, heteroaryl, substituted heteroaryl, heteroaralkyl, substituted heteroaralkyl, aralkyl or substituted aralkyl.

As used herein, the term "sulfonylamino" denotes the group —NR$^q$S(O)$_2$— where R$^q$ is hydrogen or lower alkyl.

As used herein, the term "substituted sulfonylamino" denotes the group —NR$^q$S(O)$_2$R$^u$, where R$^q$ is hydrogen or lower alkyl and R$^u$ is lower alkyl, substituted lower alkyl, cycloalkyl, substituted cycloalkyl, heterocyclyl, substituted heterocyclyl, aryl, substituted aryl, heteroaryl, substituted heteroaryl, heteroaralkyl, substituted heteroaralkyl, aralkyl or substituted aralkyl.

As used herein, the term "sulfuryl" refers to substituents of the structure =S(O)$_2$.

As used herein in connection with numerical values, the terms "approximately" and "about" mean 10% of the indicated value.

DETAILED DESCRIPTION OF THE INVENTION

Figure 1:
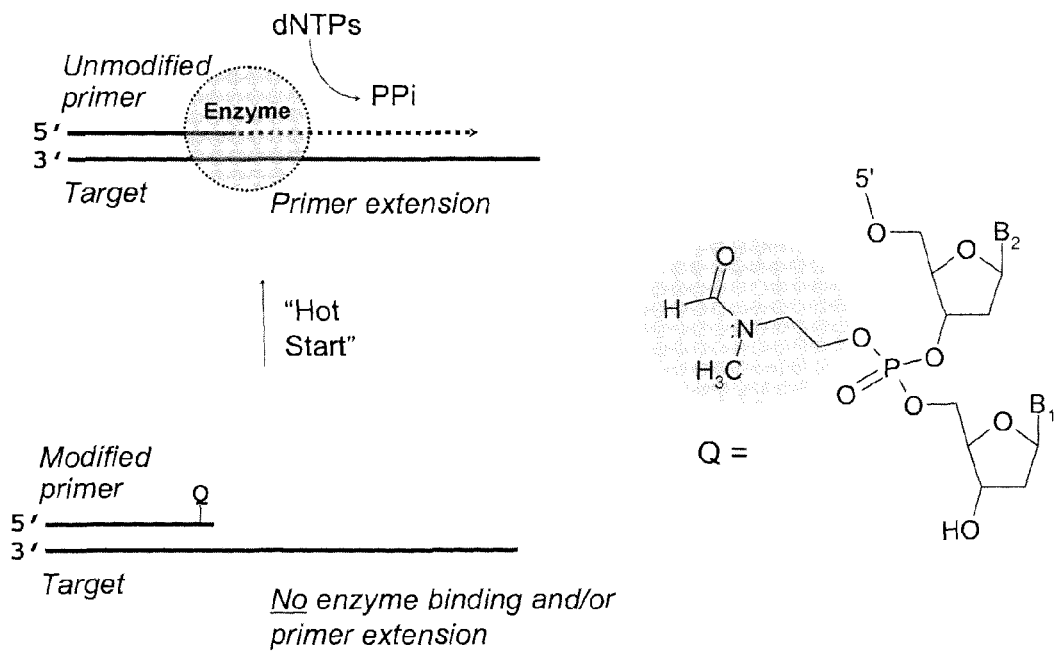
FIG. 1 is a schematic representation of the chemical modification (Q) impairing DNA polymerase mediated oligonucleotide primer extension prior to "hot start" activation.
Figure 2:
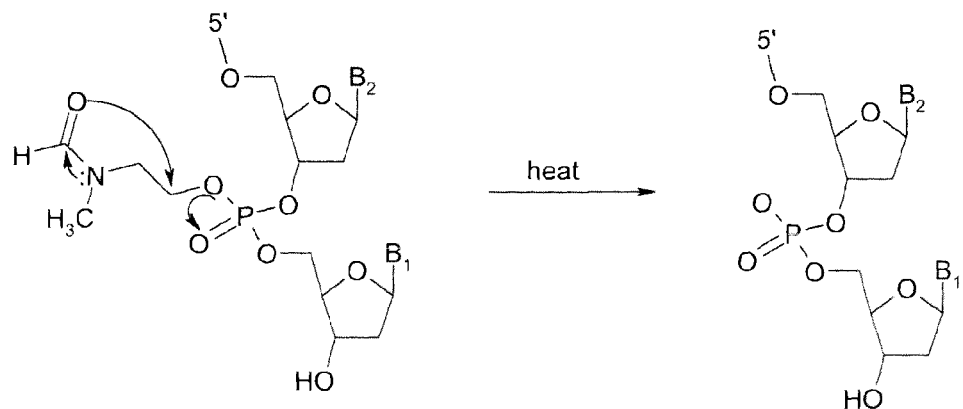
FIG. 2 is a schematic representation of the likely mechanism for thermally induced intramolecular fragmentation by which a phosphotriester linkage converts to an unmodified, active state phosphodiester linkage at the 3' terminus which is extendable by polymerase.

A nucleic acid amplification reaction such as PCR involves hybridization of an oligonucleotide primer to a target nucleic acid by which deoxynucleotide triphosphates (dNTPs) are incorporated by a polymerase to form multiple copies of a target sequence. However, the amplification reaction often yields unwanted products due to mis-priming and primer dimer formation which affect the efficiency and accuracy of the procedure. Many unwanted products are produced during the initial temperature increase of the amplification reaction.

The present invention provides improved methods and compositions for nucleic acid amplification. In particular aspects, the invention is directed to the use of amplification oligonucleotide primers in temperature dependent nucleic acid amplification reactions. In certain aspects, amplification oligonucleotide primers may employ a heat-removable modification group preferably at the 3' terminus which impairs the formation of undesired amplification products.

A few strategies are based on the use of chemically-modified oligonucleotide primers. Will, et al., (U.S. Pat. No. 6,001,611) describes the use of base modifications in the primer to minimize primer-dimer formation and mis-priming. Ankenbauer, et al. (U.S. Pat. App. No. 20030119150 also published as EP1275735 and JP2003038180) describe an oligonucleotide primer blocked at the 3' terminus with a phosphate group that is removed by a thermostable 3'-5' exonuclease. Ullman, et al. (U.S. Pat. No. 6,482,590) discloses an oligonucleotide primer that is modified at the 3' terminus which is also removed by an exonuclease. Bonner, et al. (U.S. Pat. App. No. 20030162199) claims an oligonucleotide primer modified with glyoxyl at a guanosine nucleotide that is heat-reversible covalent linkage that disrupts hybridization with a target strand.

Thermolabile groups have been used and described in literature for use in the process of oligonucleotide primer synthesis. See Grajkowski, et al., 3 Org. Lett., 1287-90 (2001); Wilk. A., et al., 42 Tetrahedron Lett., 5635-39 (2001); Wilk, A., et al., 67 J. Org. Chem., 6430-38 (2002); Cieslak, J., et al., 68 J. Org Chem., 10123-29 (2003); Cieslak, J., et al., 69 J. Org. Chem., 2509-15 (2004); and Beaucage et al., U.S. Pat. No. 6,762,298.

In one aspect, the invention provides a method of amplifying nucleic acids, the method including amplifying nucleic acid using a modified oligonucleotide primer, where the modified oligonucleotide primer includes one or more modification groups at the 3' terminus. The modification group dissociates during the initial denaturation step of the amplification. In one embodiment, the modification group includes one or more of the following chemical groups of Formula I, Formula Ia, Formula Ib, Formula Ic, Formula Id, Formula II, Formula III and/or Formula IV as further described herein.

In preferred embodiments, the invention provides a modified oligonucleotide primer which is an oligonucleotide primer that possesses at least one nucleotide with a modification group at the 3'-terminus thereof as compared to an oligonucleotide primer having an active state or unmodified nucleotide at its 3'-terminus. For the purpose of defining the position of a modified nucleotide, 3'-terminus includes any of the last six nucleotides at the 3'-terminus of the oligonucleotide primer, preferably any of the last three nucleotides. A modified nucleotide is unable to chain extend, i.e., not extendable, along a polynucleotide to which it is hybridized, either through inhibition of the enzyme or through decreased hybridization to the target nucleic acid. Accordingly, chain extension does not occur to any substantial degree unless and until the modification or the modified nucleotide is removed. The modification impairs DNA polymerase mediated oligonucleotide primer extension prior to the initial incubation period at an elevated temperature of amplification such as in PCR. Oligonucleotide primers of the present invention have two states. First, the oligonucleotide primer population is in an inactive state until the initial denaturation temperature is reached, often 95° C. but can be between about 80-105° C., more preferably between about 85-100° C., more preferably between about 90-96° C. Upon reaching the initial denaturation temperature, the oligonucleotide primer becomes active by thermally induced intramolecular fragmentation which converts a modified oligonucleotide primer to the corresponding unmodified oligonucleotide primer. This second state of the oligonucleotide primer has an active state phosphodiester bond and is extendable by polymerase. Partial or complete dissociation of the modification group preferably occurs after incubation, at about 95° C., with $t_{1/2}$ between about 0.1-120 minutes but can occur between about 1-120 minutes, 2-90 minutes, preferably between about 2-60 minutes, preferably between about 2-40 minutes, preferably between about 2-30 minutes, preferably between about 2-5 minutes, preferably between about 4 minutes, more preferably between about 3 minutes and even more preferably in about 2 minutes. In certain embodiments, dissociation occurs in respect to temperature and does not require enzymes, chemicals, or amplification reaction conditions such as pH.

Modified oligonucleotide primers of the present invention have two states. The first state of the modified oligonucleotide primer is in an inactive state due to the presence of a modification group until the initial denaturation temperature is reached, preferably 80° C., or preferably 85° C., or preferably 90° C., or preferably 95° C. Upon reaching the initial denaturation temperature, the oligonucleotide primer becomes active by thermally induced intramolecular fragmentation which converts the oligonucleotide to the second state. This second state of the oligonucleotide primer is the corresponding unmodified oligonucleotide primer which has an active state phosphodiester bond and is extendable by polymerase. Dissociation of the modification group preferably occurs at approximately 95° C. between about 0.1-120 minutes, or between about 1-120 minutes, or between about 2-90 minutes, or between about 2-60 minutes, or between about 2-40 minutes, or between about 2-30 minutes, 2-10 minutes, or between about 2-8 minutes, or between about 2-5 minutes; or 2 minutes, or 5 minutes or 10 minutes. In certain embodiments, dissociation occurs in respect to temperature and does not require enzymes, chemicals, or amplification reaction conditions such as pH. In another embodiment, the modification group does not dissociate from a modified oligonucleotide below about 80° C., or below about 85° C., or below about 90° C.

In another aspect, the present invention provides for an oligonucleotide primer for nucleic acid amplification where the nucleic acid sequence has one or more modification groups. Preferably, the modification group includes one or more of the following chemical groups of Formula I, Formula Ia, Formula Ib, Formula Ic, Formula Id, Formula II, Formula III and Formula IV. In a preferred embodiment, the modified oligonucleotide is between about 6-70 nucleotides in length, preferably 10-45 nucleotides in length, preferably between 15-30, more preferably between 19-29.

The modified oligonucleotide primer has at least one modified internucleotide linkage. In another embodiment, the oligonucleotide primer may comprise a contiguous sequence of 2, 3, 4 5 or 6 modified internucleotide linkages terminating at the 3'-terminus of the oligonucleotide primer. In yet another embodiment, the oligonucleotide primer may comprise multiple noncontiguous 3' modified internucleotide linkages. The 5'-terminus of the modified oligonucleotide primer may also have a sequence of nucleotides, including modified internucleotide linkages. In yet another embodiment, all internucleotide linkages of the oligonucleotide may be modified.

In another preferred embodiment, the modified oligonucleotide primer comprises a modification group at the 3' n internucleotide linkage of the oligonucleotide primer where n is the 3' terminal internucleotide linkage. In yet other embodiments, the modification group is at the 3' n-1, n-2, n-3 or n-4 internucleotide linkage of the oligonucleotide. In yet a further embodiment, the oligonucleotide has modification groups at more than one of the n, n-1, n-2, n-3, n-4, n-5 or n-6 positions; preferably two or more of the n, n-1, n-2, n-3, n-4, n-5 or n-6 positions; preferably three or more of the n, n-1, n-2, n-3, n-4, n-5 or n-6 positions; preferably four or more of the n, n-1, n-2, n-3, n-4, n-5 or n-6 positions; preferably five or more of the n, n-1, n-2, n-3, n-4, n-5 or n-6 positions, or preferably six or more of the n, n-1, n-2, n-3, n-4, n-5 or n-6 positions.

The modification group can be integrated into an oligonucleotide by using existing automated synthesis and purification methods. Oligonucleotide primers of the present invention may be synthesized by any methods well-known in the art, including automated solid-phase chemical synthesis using cyanoethylphosphoramidite precursors (Barone et al., 12 Nucleic Acids Research, 4051 (1984)), and as described in J. Sambrook, E. F. Fritsch and Maniatis, T., Molecular Cloning, ch. 11 (2d ed. 1989). Other approaches include phosphotriester and phosphodiester synthesis methods can be used (Narang, et al., Meth. Enzymol. 68-90 (1979)). A comprehensive overview of a variety of methods for the synthesis of modified and unmodified oligonucleotides can be found in Beaucage, S. L. et al., Current Protocols in Nucleic Acid Chemistry (2006). Following synthesis and purification of a modified oligonucleotide primer, several different procedures may be utilized to determine the acceptability of the oligonucleotide primer in terms of size and purity. One such procedure is polyacrylamide gel electrophoresis. Another such procedure is High Performance Liquid Chromatography ("HPLC"). These procedures are well known to those skilled in the art. Current methods employed for purification and separation in the art are applicable to the modified oligonucleotide primers of the present invention as well.

Any modification group that accomplishes the purposes of the present invention may be utilized. The modification group should be one that dissociates or is removable under conditions of the amplification reaction in which the modified oligonucleotide primer is used. On the other hand, the modification should not dissociate so fast that one cannot obtain the control of dissociation necessary to achieve the benefits of the present invention. The type and extent of modification of the 3'-terminus of the modified oligonucleotide primer is generally determined empirically with the goal of achieving the above parameters for control of dissociation of the 3'-terminus of the modified oligonucleotide primer.

While it is understood that not all oligonucleotide primers in the amplification reaction will initially be in the inactive state, preferably the mixture of oligonucleotide primer states improves specificity in a mixed population as compared to not using modified oligonucleotides at all. Preferably modified oligonucleotides comprise at least 30% of total oligonucleotides, preferably at least 70% of total oligonucleotides, preferably at least 80% of total oligonucleotides and more preferably at least 90% of total oligonucleotides. In another embodiment, only forward or only reverse oligonucleotides may be modified oligonucleotides. In reactions with only one orientation of modified oligonucleotides, such as forward oligonucleotides, the modified oligonucleotides comprise at least 50% of total forward oligonucleotides, or at least 60% of total forward oligonucleotides, or at least 70% of total forward oligonucleotides, or at least 80% of total forward oligonucleotides, or at least about 90% of total forward nucleotides.

In one aspect, the present invention provides a chemically modified phosphoramidite with a modification group which is removable by heat when the corresponding oligonucleotide is formed. Each phosphoramidite can be modified with a thermnolabile group which in turn can be used in oligonucleotide primer synthesis which are compatible with current synthesis methods. The modified phosphoramidite can be added to any position of the oligonucleotide primer. In contrast, glyoxyl modification can only be added to guanine (dG). Therefore location of modification depends on the sequence of the oligonucleotide primer. Oligonucleotides of the present invention, can have modification groups specifically added to any desired position or positions.

In yet another aspect, the present invention provides a primer containing nucleoside analogs, as described herein.

Thermus aquaticus (Taq) DNA polymerase, a thermal-stable polymerase, as well as other DNA polymerases do not readily extend oligonucleotide primers having one or more methylphosphonate modified internucleotide linkages at their 3' termini. Sauer, et al. 30 Nucleic Acids Res., e22 (2002). While internucleotide methylphosphonate linkages (FIG. 1) would not be predicted to undergo thermally-induced conversion to an active state phosphodiester linkage in neutral aqueous media, alternative modification as in the present invention, can be designed to do so based on steric and electronic factors.

One aspect of the present invention provides a chemically modified oligonucleotide primer with a protecting group removable by heat in temperatures compatible with amplification procedures currently in use. The modification group may impair base pairing with a target sequence or inhibits polymerase extension. The oligonucleotide primer is not extendable by polymerase until the amplification reaction reaches an optimal temperature which coincides with the initial denaturation step of PCR and significantly decreases unwanted amplification products.

In addition to being stable at room temperature, the modification group is stable in conditions for oligonucleotide primer synthesis, separation processes such as chromatography, purification processes such as alcohol precipitation, long term storage and amplification reaction preparation. Modified oligonucleotides are preferably stored as a solid or in DMSO solution at −80° C., −20° C., 4° C. or room temperature.

In another embodiment, oligonucleotide primers of the present invention with the modification group is substantially chirally pure (Rp or Sp). Separation techniques have been described by Stec, et al., 26 Tetrahedron Lett., 2191-2194 (1985), Gallo, et al., 14 Nucleic Acids Res., 7405-7420 (1986), Koziolkiewicz, et al., 26 Chem. Scripta, 251-60 (1986) and LaPlanche, et al., 14 Nucleic Acids Res., 9081-93 (1986).

In another embodiment, oligonucleotides primers of the present invention with or without the modification group are complementary to the target nucleic acid of interest. Preferably the oligonucleotide primer is at least 75%, at least 85%, at least 85%, at least 90%, at least 95%, and more preferably at least 98% complementary to the target nucleic acid.

The invention also provides for kits containing a modified oligonucleotide primer. For example, kits containing PCR reagents as well as modified oligonucleotide primers for common amplification targets such as housekeeping genes. The kit may comprise one or more nucleic acid amplification reagents selected from the group consisting of reaction buffer. dNTPs, magnesium, polymerase and modified oligonucleotide primers. Preferably the kit comprises two or more nucleic acid amplification reagents, preferably three or more and more preferably four or more.

The invention also provides for modified phosphoramidite reagents for solid phase primer synthesis. These reagents will be sold individually or in sets. These reagents may include the phosphoramidites of the four natural deoxynucleotides (dA, dC, dG, and dT) modified with one of the described modification group(s). Reagents may also include phosphoramidites of nuceleoside analogs, as defined herein.

The invention also provides for solid support reagents for use in solid phase primer synthesis. These solid supports will contain at least two attached nucleotides, with internucleotide modification groups of Formula I, Ia, Ib, Ic, Id, II, III or IV at all possible positions along the oligonucleotide.

The invention will now be described in greater detail by reference to the following non-limiting examples.

Example 1

Synthesis of Nucleoside Phosphoramidites

A first step to synthesizing a modified nucleoside phorphoramidite is to react bis (diisopropylamino) chlorophosphine with the alcohol precursor of the desired modification group. The resultant monoesterified product is reacted with the appropriately protected nucleoside in the presence of diisopropylammonium tetrazolide as a catalyst to generate the modified nucleoside phosphoramidite. Although N-(2-hydroxyethyl) phthalimide, 4-oxo-1-pentanol, and 4-methylthio-1-butanol alcohols are commercially available, 3-(N-tert-butylcarboxamido)-1-propanol can be prepared according to procedure published by Wilk, A., et al, 67 J. Org. Chem., 6430-38 (2002)

In anticipation of low stability of the phosphotriester fragment in the synthesized oligonucleotide primers, the nucleoside bases were protected with either an ultra mild or traditional protecting groups, where the ultra mild base protecting group included phenoxyacetyl for adenine and cytosine and iso-propyl-phenoxyacetyl for guanine.

Upon production of modified phosphoramidites for 2'-deoxyadenosine, 2'-deoxycytosine, 2'-deoxygunosine, and 2'-deoxythymidine, model tetranucleotide sequences containing a single 3'-internucleotide PTE group were synthesized. The coupling between the modified phosphoramidite and a 5'-OH nucleoside attached to a CPG support can be performed manually or by an automated synthesis machine. In this instance the 8909 Expedite Synthesizer was used in accordance with manufacturer's suggested protocols.

The tetranucleotide 3'-phosphotriester derivatives were deprotected and cleaved from CPG support by treatment with 50 mM potassium carbonate in methanol for several hours. Reverse phase HPLC purification (with the gradient of acetonitrile in triethylammonium acetate buffer (pH 7.2)) was used for isolation of the 3'-phosphotriester tetranucleotides containing 4-methylthio-1-butanol (MTB), 4-oxo-1-pentanol (OXP), and 3-(N-tert-butylcarboxamido)-1-propanol (TBCA) groups. In most cases, the conditions used during the synthesis, deprotection and cleavage from the support, resulted in a partial loss of PTE function (for the N-(2-hydroxyethyl) phthalimido PTE group, EPH, complete deprotection occurred during these steps). With further optimization, the degree of degradation of the PTE functionality may be significantly diminished. Each of the isolated 3'-phosphotriester tetranucleotides were shown to be stable for several months when kept in frozen solution at −70° C. In addition to the tetranucleotide sequences, longer PTE-protected oligonucleotide sequences suitable for PCR were also prepared. Example are provided in Table 1 below.

TABLE 1

Synthesized Deoxyoligonucleotides

| Sequence (5' to 3') | PTE group | Description |
|---|---|---|
| GCAT (SEQ ID NO: 1) | TBCA | model |
| GCAT (SEQ ID NO: 2) | MTB | model |
| GACT (SEQ ID NO: 3) | TBCA | model |
| GCAT (SEQ ID NO: 4) | OXP | model |
| GACT[a] (SEQ ID NO: 5) | EPH | model |
| GAA TTG GGT GTC AAC ATA GCA GAA T (SEQ ID NO: 6) | OXP | HIV[b] primer 1 |
| GAA TTG GGT GTC AAC ATA GCA GAA T (SEQ ID NO: 7) | None | HIV primer 1 |
| AAT ACT ATG GTC CAC ACA ACT ATT GCT (SEQ ID NO: 8) | OXP | HIV primer 2 |
| AAT ACT ATG GTC CAC ACA ACT ATT GCT (SEQ ID NO: 9) | None | HIV primer 2 |
| AAG GAG CTG GCT GAC ATT TTC G (SEQ ID NO: 10) | OXP | Lambda DNA[c] primer 1 |
| AAG GAG CTG GCT GAC ATT TTC G (SEQ ID NO: 11) | None | Lambda DNA primer 1 |
| CGG GAT ATC GAC ATT TCT GCA CC (SEQ ID NO: 12) | OXP | Lambda DNA primer 2 |
| CGG GAT ATC GAC ATT TCT GCA CC (SEQ ID NO: 13) | None | Lambda DNA primer 2 |
| TAA TGC CTA TTC TGC TAT GTT GGC ACC CAA TTC TTT TTT T (SEQ ID NO: 14) | None | HIV template 1 |
| AAT CTT AGC AAT AGT TGT GTG GAC CAT AGT ATT TTT TTT T (SEQ ID NO: 15) | None | HIV template 2 |

[a] complete loss of the PTE group occurred during deprotection
[b] HIV target: Gene Amplimer HIV-1 control reagents kit (Applied Biosystems)
[c] Lambda DNA target: Clone 857 Sam 7 (Roche)

Example 2

Kinetic Conversion of a PTE Modified Oligonucleotide to the Corresponding PDE Sequence The kinetics of deprotection of the 3'-phosphotriester (PTE) modified tetranucleotide sequences to the corresponding phosphodiester (PDE) sequence were investigated at "neutral" pH (in mixture of acetonitrile triethylammonium acetate, pH 7.2) or in PCR buffer (pH 8.4 at 25° C.) at 20° C., 50° C., and 95° C. In both buffers, similar deprotection kinetics were evident for the PTE-containing oligonucleotide primers.

The $t_{1/2}$ for the conversion of the PTE-modified oligonucleotide primer to the corresponding PDE sequence was determined to range from >1 minute to 10 minutes at 95° C. for the OXP, MTB, and TBCA tetranucleotide 3'-phosphotriester derivatives. At a lower temperature (50° C.), the deprotection kinetics were slower, with $t_{1/2}$ ranging from 10 to 105 minutes. At room temperature (20° C.), the $t_{1/2}$ was between 3 and >100 hours. For suitable application in Hot Start PCR technologies, the PTE groups should optimally be stable during synthesis and deprotection conditions (20° C.) and be readily removable at elevated temperatures (95° C.).

Example 3

Large-Scale Synthesis of Phosphoramidites

Figure 3:
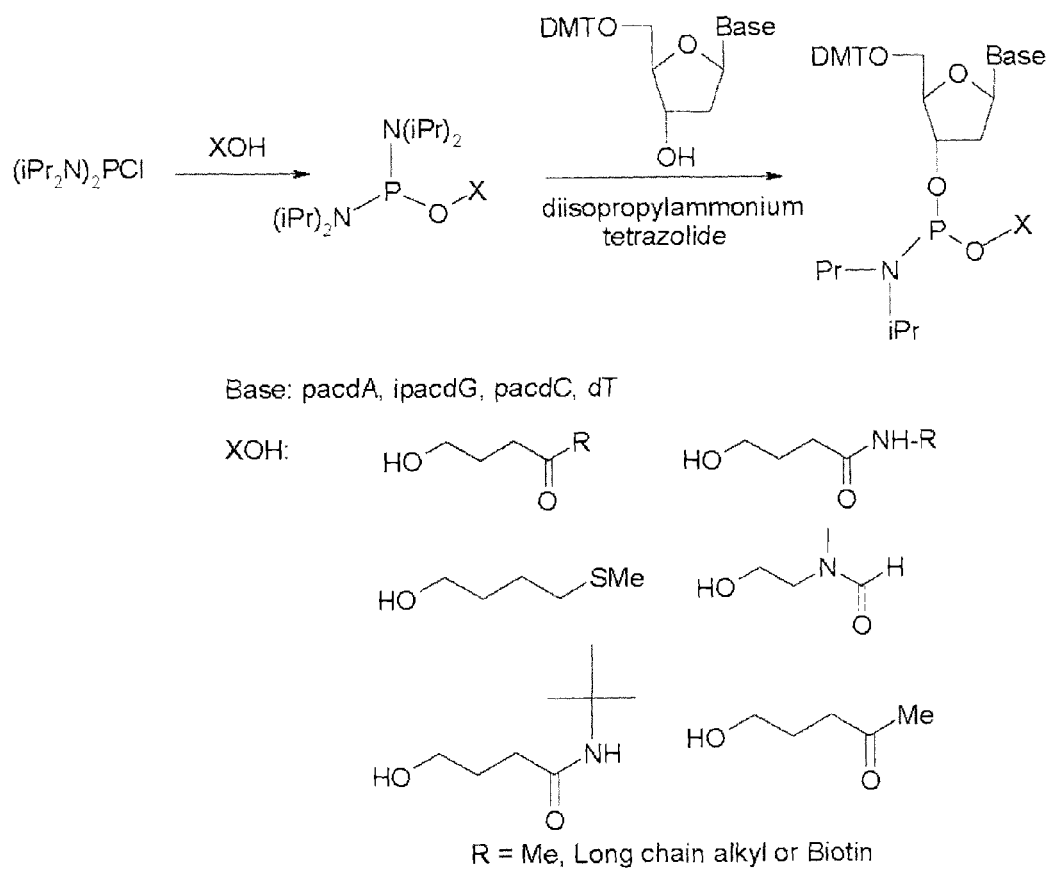
FIG. 3 is a general synthetic scheme for modifying oligonucleotide priners with phosphoramidite derivatives.

For the scale-up synthesis, and preparation of multi gram quantities (5 g starting scale) of the protected 3'-phosphoramidites of dA, dG, dC and dT, using the two step-one pot procedure shown in FIG. 3. As before, ultra mild protecting groups were used for exocyclic amino group of the nucleoside bases. The 5'-DMT protected nucleoside 3'-phosphoramidites were isolated by silica gel chromatography in 50-70% overall yield and as a solid were shown to be stable at room temperature for at least two weeks. It is anticipated that the nucleoside 3'-phosphoramidite should be stable for low temperature storage (between about −70° C. to −100° C.) for at least one year.

Example 4

PTE and PDE DNA Polymerase Extension Comparison

For HIV-1 (Q. Chou, et al.) and Lambda DNA targets, a series of forward and reverse oligonucleotide primers were prepared, which contained PTE modifications. For each target, one set contained a phosphotriester group at 3'-internucleotide linkage and the other set contained the active state phosphodiester linkage at the corresponding position. These oligonucleotide primers were chosen because the unmodified, PDE oligonucleotide primers were shown to form primer-dimers during PCR. The first coupling between the modified phosphoramidite and the 5'-OH nucleoside attached to a CPG-solid support was performed manually, while the remainder of the synthesis was performed on 8909 Expedite Synthesizer using manufacturer's suggested protocols (at 1 µmole scale). The oligonucleotide primers were deprotected and cleaved from polymer support using 50 mM potassium carbonate in methanol. Reverse phase HPLC purification (with a gradient of acetonitrile in triethylammonium acetate buffer (pH 7.2)) allowed for successful purification and isolation of the 3'-phosphotriester modified oligonucleotide primers. The isolated PTE oligonucleotide primers were shown to be stable for several months when kept in frozen solution at −20° C.

The isolated PDE and PTE primers were annealed to complementary templates and subjected to DNA polymerase extension experiments. As a control in these experiments, aliquots of the PDE and PTE primers were heated at 95° C. for the required amount of time for PTE group removal and included in primer extension experiments. Primer extension experiments were performed at room temperature for both Klenow fragment DNA polymerase I and Taq DNA polymerase, to avoid extensive loss of PTE functionality. To monitor the kinetics of primer extension, aliquots were taken at the specified time intervals over a 2 to 80 minute period and were quenched on dry ice by the addition of EDTA. The extension progress was assessed by denaturing polyacrylamide gel electrophoresis. Interestingly, unheated, PTE-modified primers were found to migrate more slowly during gel electrophoresis than the corresponding PDE oligonucleotide primers (heated and non-heated) and heated PTE oligonucleotide primers.

The abilities of Taq DNA polymerase and Klenow fragment of DNA polymerase I to perform template-dependant elongation of 3'-PTE modified oligonucleotide primer (and non-modified PDE control oligonucleotide primers) were investigated. Under the amplification reaction conditions, it was found that a standard PDE primer can be elongated to a full-length extension product while PTE oligonucleotide primers are very poorly extended by Klenow fragment DNA polymerase I. During the timeframe of the primer extension reactions, there was a slight accumulation of truncated extension products for reactions containing the PTE oligonucleotide primer, an occurrence which may be attributed to either partial deprotection of the PTE oligonucleotide primer during the extension reaction or to preferential extension of one PTE stereoisomer. When the PDE and PTE oligonucleotide primers were preheated at 95° C., the extension of the oligonucleotide primer is no longer hindered and is consistent with a PDE oligonucleotide primer. Although the most detailed extension experiments were performed with the mesophilic Klenow fragment of DNA polymerase I, similar results were obtained with the thermophilic Taq DNA polymerase, a DNA polymerase suitable for PCR. Overall, the extendibility of PTE containing oligonucleotide primers was significantly reduced relative to the corresponding active state PDE oligonucleotide primer, an essential criterion for a "hot start" PCR oligonueleotide primer of the present invention.

Example 5

Performance of PTE Oligonucleotide Primers in Template-Independent PCR

Due to poor extendibility of the PTE oligonucleotide primer in the oligonucleotide primer extension experiments (Example 4), it was concluded that PTE oligonucleotide primers should greatly diminish the amount of primer-dimer formed during sample preparation and the initial heating step of PCR by restricting DNA polymerase extendibility. To further explore the effect of the PTE-modified group on primer-dimer formation, PCR conditions that generate primer dimers in high yields in the absence of template were evaluated. Therefore, PTE-modified oligonucleotide primers targeted to the tat HIV-1 gene were preheated at 95° C. in PCR buffer (pH 8.4 at 25° C.) for increasing amounts of time prior to PCR amplification by Taq DNA polymerase. By preheating the PTE primers for incremental amounts of time, the effect of PTE modification on primer dimer formation can be evaluated. Primer dimers, which were detected by agarose gel electrophoresis, ran as a 50-80 base pair fragment.

For the HIV-1 oligonucleotide primer pair, the oligonucleotide primer concentration for formation of primer-dimers was 4.5 µM, approximately 5-fold higher than generally recommended and the PCR cycling parameters included: 95° C. for 2 min; 30 cycles of [95° C. for 40 sec; 56° C. for 30 sec; 72° C. for 2 min]; 72° C. for 7 min. During the pre-PCR heating treatment of the corresponding PTE oligonucleotide primers prior to PCR set-up, the amount of PDE oligonucleotide primer generated should be proportional to the time the PTE oligonucleotide primers were pre-heated. We found that as the fraction of PDE oligonucleotide primers formed increases, so does the chance of forming primer-dimers during PCR. For pre-incubation times up to 0-40 minutes, the amount of primer dimer formed is proportional to the time of pre-PCR heating, and the proportion positively correlates with the kinetics of the conversion of the PTE oligonucleotide primer to the PDE oligonucleotide primer at 95° C. However, when PTE oligonucleotide primers undergo extensive preheating treatment (80 and 150 minutes), the amount of the primer dimer formation decreases, a possible consequence of oligonucleotide primer degradation by depurination. Overall, the level of oligonucleotide primer dimer formation in PCR was significantly diminished by the use of PTE-oligonucleotide primers.

Example 6

Performance of PTE Oligonucleotide Primers in PCR

For the Lambda DNA and HIV-1 DNA primer, PCR conditions were identified that efficiently formed primer-dimers with the unmodified, PDE oligonucleotide primers in the presence of template. Using oligonucleotide primers targeted to HIV and Lambda DNA templates, the optimal conditions for efficient formation of primer dimers in the presence of template employed 1-2 µM concentration of both the forward and forward oligonucleotide primers, 5-40,000 copies of template, and 1.5 to 2.0 mM $MgCl_2$. PCR cycle parameters were used as follows: 95° C. for 2 min; 40 cycles of [95° C. for 40 sec; 56° C. for 30 sec; 72° C. for 2 min]; 72° C. for 7 min. The progress of the reaction was monitored by removing aliquots after cycles 30, 35, and 40 and analyzing them by agarose gel electrophoresis.

For both the Lambda and HIV-1 DNA targets, the unheated PTE modified oligonucleotide primers (PTE 0° C.) were found to greatly improve the outcome of PCR in comparison to the unheated, unmodified PDE oligonucleotide primers (PDE 0° C.). In each case, the unheated PTE oligonucleotide primers showed a remarkable decrease in the amount of primer-dimer formation and a corresponding increase in amplicon formation.

To ensure that improved results of PTE oligonucleotide primers in PCR were not due to any differences in the preparation and handling of the PDE and the PTE oligonucleotide primers, the PTE oligonucleotide primers were preheated in PCR buffer for conversion to the corresponding PDE oligonucleotide primer. Subsequently, the heated PTE oligonucleotide primers (PTE 95° C.) and heated PDE oligonucleotide primers (PDE 95° C.) were employed in PCR, and it was found that primer dimers formed to a similar if not greater extent to the unheated PDE oligonucleotide primers. Integration of the amplicon and primer dimers bands for the Lambda DNA and HIV system (for cycle 35) revealed a much higher ratio of amplicon to primer dimer for the unheated PTE oligonucleotide primers, in comparison to PCR amplifications that were performed with either PDE oligonucleotide primers or with heated PTE oligonucleotide primers. When the ratio of amplicon to primer dimer for all amplification reactions were normalized to the ratio for the unheated PTE oligonucleotide primer, a marked improvement in PCR specificity for amplicon formation was seen for both the Lambda DNA and for the HIV-1 DNA systems. The PTE oligonucleotide primer caused between a 2.6 and a 15-fold improvement in PCR performance. Overall, the utility of the hot start PTE oligonucleotide primers of the present invention in PCR has been demonstrated as, in comparison to the PDE oligonucleotide primers. The amount of primer dimer decreased significantly, with a concurrent increase in amplicon production.

Example 7

Performance of PTE Oligonucleotide Primers in Reverse-Transcriptase PCR

PTE-modified primers were prepared for a two-step RT-PCR system used for detection of housekeeping gene porphobilinogen deaminase (PBGD) as described by Kielar, D., et al., 47 Clinical Chemistry 2089-2097(2001). Forward primers with SEQ ID NO:16 (5'-GAGTGATTCGCGTGGG-TACC) and reverse primers with SEQ ID NO:17 (5'-GGCTC-CGATGGTGAAGCC) were made containing two PTE modifications per primer at the two 3'-terminal positions. Detection of a 264 bp amplicon product was used to validate a two-step protocol system.

The two-step protocol included reverse transcription, followed by PCR amplification. The reverse transcription conditions utilized 0.4 µM oligo(dT) primer, 0 or 1 µg of human liver total RNA, and 15 U of Cloned AMV reverse transcriptase in a 20 µL reaction. The reaction was subjected to the following reverse transcriptase thermal cycling protocol: 25° C. for 10 min; 42° C. for 60 min; and 95° C. for 5 min. After completion, the reverse transcription product was diluted 1 in 10 and was used as the template for a series of PCR reactions. Two sets of PCR reactions were prepared. The first set contained unmodified PDE primers at 0.5 µM, and the second set contained PTE modified primers at 0.5 µM. Each set of reactions contained three reactions, each of which utilized different templates: reaction a) water, reaction b) 0 µg Human liver total RNA reverse transcription product, and reaction c) 1 µg human liver total RNA reverse transcription product. All PCR reactions contained 1.25 U of Taq DNA polymerase and were 50 µL in volume. The mixtures were subjected to thermal cycling protocol: 94° C. for 10 min; [94° C. for 30 sec, 60° C. for 30 sec, 72° C. for 30 sec] 40 times. The reaction products were then analyzed by agarose gel analysis. Reactions a) and b) from both sets functioned as negative controls. For the negative controls, unmodified, PDE primers formed a significant amount of primer dimer, while the modified, PTE primers displayed no detectable primer dimer formation. For both the PDE and the PTE primers, reaction c) formed the desired 264 bp product. However, as was evident for the negative controls, the PDE primer reactions contained a significant amount of primer dimer formation, while the PTE primer reactions did not. Overall, the benefit of PTE-modified primers in two-step RT-PCR is evident, the modified primers suppressed formation of undesired primer dimers.

The same primer pairs were also utilized in a one-step RT-PCR protocol. As in the two-step protocol, two sets of reactions were prepared. The first set contained unmodified PDE primers at 0.5 µM, and the second set contained PTE modified primers at 0.5 µM. Each set consisted of three reactions, with reactions b) and c) as negative controls. Reaction a) consisted of 0.25 µg of human liver total RNA and 25 U of MMLV reverse transcriptase, reaction b) consisted of 0.25 µg of human liver total RNA and 0 U of MMLV reverse transcriptase, and reaction c) consisted of 0 µg of human liver total RNA and 25 U of MMLV reverse transcriptase. The reactions all contained oligo(dT) primers at 5 µM and 0.3 U of Taq DNA polymerase and were at a volume of 25 µL. The reactions were incubated as follows: 42° C. for 60 min; 94° C. for 5 min; [94° C. for 30 sec, 60° C. for 30 sec, 72° C. for 5 min] 30 times; and 72° C. for 5 min. The reaction products were analyzed by agarose gel electrophoresis. For both primer pairs, the no RT controls, b), appeared the same, with a slight smudge appearing on the gel, which is likely due to the presence of total RNA in the samples. For the no RNA controls c), the PDE primers displayed a low molecular weight primer dimer band, while the PTE primers did not display any detectable amplification product. The low molecular weight primer dimer band is likely due to reverse-transcriptase-mediated extension of the PDE PCR primers, as has been discussed by Peters, I.R., et al., 286 Journal of Immunological Methods 203-217 (2004). For reaction a), both primer pairs formed the desired 264 bp product. However, the reaction product for the PDE primers contained several amplification products, including the primer dimer band seen in reaction b), while the PTE primers formed the desired reaction product without any additional amplification products. The use of PTE-modified primers in sequential enzymatic reactions, such as one-step RT-PCR allows for the gene specific primers to be partially or completely blocked from extension during the lower-temperature reverse transcription reaction.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control Other embodiments are set forth within the following claims.

That which is claimed is:

1. A method of amplifying nucleic acids, said method comprising:

amplifying nucleic acid using a modified oligonucleotide primer, wherein said modified oligonucleotide primer comprises a modification group at one or two internucleotide linkages; wherein said modification groups are at the n, n-1, n-2, or n-3 positions, wherein n is the 3' terminal internucleotide linkage; wherein the presence of said modification group impairs nucleic acid polymerase extension of said modified oligonucleotide primer;

wherein said modification group can be non-reversibly thermally dissociated; and wherein said modified oligonucleotide primer has structure I as follows

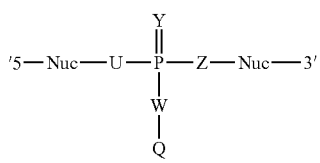

wherein:

Nuc is a nucleoside within the primer sequence;

U and Z are independently O, S, Se, $NR^9$, or $CR^9R^{10}$;

$R^9$ and $R^{10}$ are each independently hydrogen or optionally substituted straight or branched hydrocarbyl having from 1-20 carbon atoms, wherein each may independently include at least one substituent selected from halo, oxo, hydroxyl, alkoxy, aryloxy, amino, amido or a detectable label;

Y is O, S or Se;

W is O, S, S(O), $S(O)_2$, Se, C(O), C(S), C(O)NH, NH or $NR^9$; and

Q is a modification group comprising one or more thermally cleavable groups.

2. The method of claim 1, wherein said modification group, Q, comprises one or more modification groups selected from the group consisting of -L-X—$R^1$ (Formula I)

wherein:

L is a straight or branched hydrocarbylene group having between 1-10 carbon atoms;

X is O, S, S(O), $S(O)_2$, C(O), C(S) or C(O)NH; and $R^1$ is hydrogen or a straight or branched hydrocarbylene group having from 1-20 carbon atoms, which may optionally include at least one substituent selected from the group consisting of halo, oxo, hydroxyl, alkoxy, amino, amido, cycloalkyl, heterocycloalkyl, aryl, aryloxy, and heteroaryl;

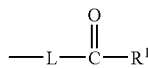

(Formula Ia)

wherein:

L is a straight or branched hydrocarbylene group having between 1-10 carbon atoms; and $R^1$ is hydrogen or a straight or branched hydrocarbylene group having from 1-20 carbon atoms, which may optionally include at least one substituent selected from the group consisting of halo, oxo, hydroxyl, alkoxy, amino, amido, cycloalkyl, heterocycloalkyl, aryl, aryloxy and heteroaryl;

-L-S(O)$_k$—$R^1$ (Formula Ib)

wherein:

k is an integer from 0-2;

L is a straight or branched hydrocarbylene group having between 1-10 carbon atoms; and $R^1$ is hydrogen or a straight or branched hydrocarbylene group having from 1-20 carbon atoms, which may optionally include at least one substituent selected from the group consisting of halo, oxo, hydroxyl, alkoxy, amino, amido, cycloalkyl, heterocycloalkyl, aryl, aryloxy, and heteroaryl;

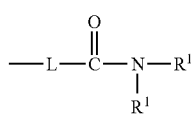

(Formula Ic)

wherein:

L is a straight or branched hydrocarbylene group having between 1-10 carbon atoms; and Each $R^1$ is independently hydrogen or a straight or branched hydrocarbylene group having from 1-20 carbon atoms, which may optionally include at least one substituent selected from the group consisting of halo, oxo, hydroxyl, alkoxy, amino, amido, cycloalkyl, heterocycloalkyl, aryl, aryloxy, and heteroaryl;

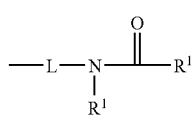

(Formula Id)

wherein:

L is a straight or branched hydrocarbylene group having between 1-10 carbon atoms; and $R^1$ is hydrogen or a straight or branched hydrocarbylene group having from 1-20 carbon atoms, which may optionally include at least one substituent selected from the group consisting of halo, oxo, hydroxyl, alkoxy, amino, amido, cycloalkyl, heterocycloalkyl, aryl, aryloxy, and heteroaryl;

-L-$R^2$ (Formula II)

wherein:

L is a straight or branched hydrocarbylene group having between 1-10 carbon atoms; and R² is hydrogen, cyano, or an optionally substituted carbocycle, heterocycle, aryl or heteroaryl having between 5-10 atoms;

$$-L^a-A-L^b-B \quad \text{(Formula III)}$$

wherein:
$L^a$ and $L^b$ are each independently selected from a bond or a straight or branched hydrocarbylene group having between 1-8 carbon atoms;
A is O, S, S(O), S(O)₂, Se, CR³R⁴, NR³, C(O), C(S) or CNR³;
B is C(O)R³, C(S)R³, C(O)NR³R⁴, OR³ or SR³; and
R³ and R⁴ are each independently hydrogen or straight or branched hydrocarbylene group having from 1-20 carbon atoms, which may optionally include at least one substituent selected from the group consisting of halo, oxo, hydroxyl, alkoxy, amino, amido, cycloalkyl, heterocycloalkyl, aryl, aryloxy, and heteroaryl; and $$-L^a-D-L^b-E-L^c-F \quad \text{(Formula IV)}$$

wherein:
$L^a$, $L^b$ and $L^c$ are each independently selected from a bond or a straight or branched hydrocarbylene group having between 1-8 carbon atoms;
D is O, S, S(O), S(O)₂, CR⁵R⁶, and NR⁵;
E is O, S, S(O), S(O)₂, CR⁵R⁶, and NR⁶;
F is hydrogen, C(O)R⁷, C(S)R⁷, C(O)NR⁷R⁸, OR⁷ and SR⁷;
R⁵ and R⁶ can each independently be hydrogen, aryl, alkyl, halo, oxo, hydroxyl, alkoxy, aryloxy or amino, or R⁵ and R⁶ can cooperate to form a mono or bicyclic ring consisting 5-10 atoms and including D, R⁵, R⁶, E and $L^b$, provided that when R⁵ and R⁶ cooperate to form a ring, n is from 0-2; and
R⁷ and R⁸ are each independently selected from the group consisting of aryl, alkyl, halo, oxo, hydroxyl, alkoxy, aryloxy, amino, amido, optionally substituted cycloalkyl, optionally substituted heterocycloalkyl, optionally substituted aryl, optionally substituted aryloxy, and optionally substituted heteroaryl.

3. The method of claim 1, wherein said modification group, Q, comprises:

$$-L-X-R^1 \quad \text{(Formula I)}$$

wherein:
L is a straight or branched hydrocarbylene group having between 1-10 carbon atoms;
X is O, S, S(O), S(O)₂, C(O), C(S) or C(O)NH; and
R' is hydrogen or a straight or branched hydrocarbylene group having from 1-20 carbon atoms, which may optionally include at least one substituent selected from the group consisting of halo, oxo, hydroxyl, alkoxy, amino, amido, cycloalkyl, heterocycloalkyl, aryl, aryloxy, and heteroaryl.

4. The method of claim 1, wherein said modification group, Q, comprises:

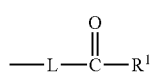
(Formula Ia)

wherein:
L is a straight or branched hydrocarbylene group having between 1-10 carbon atoms; and
R¹ is hydrogen or a straight or branched hydrocarbylene group having from 1-20 carbon atoms, which may optionally include at least one substituent selected from the group consisting of halo, oxo, hydroxyl, alkoxy, amino, amido, cycloalkyl, heterocycloalkyl, aryl, aryloxy, and heteroaryl.

5. The method of claim 1, wherein said modification group, Q, comprises:

$$-L-S(O)_k-R^1 \quad \text{(Formula Ib)}$$

wherein:
k is an integer from 0-2;
L is a straight or branched hydrocarbylene group having between 1-10 carbon atoms; and
R¹ is hydrogen or a straight or branched hydrocarbylene group having from 1-20 carbon atoms, which may optionally include at least one substituent selected from the group consisting of halo, oxo, hydroxyl, alkoxy, amino, amido, cycloalkyl, heterocycloalkyl, aryl, aryloxy, and heteroaryl.

6. The method of claim 1, wherein said modification group, Q, comprises:

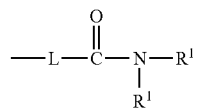
(Formula Ic)

wherein:
L is a straight or branched hydrocarbylene group having between 1-10 carbon atoms; and
Each R¹ is independently hydrogen or a straight or branched hydrocarbylene group having from 1-20 carbon atoms, which may optionally include at least one substituent selected from the group consisting of halo, oxo, hydroxyl, alkoxy, amino, amido, cycloalkyl, heterocycloalkyl, aryl, aryloxy, and heteroaryl.

7. The method of claim 1, wherein said modification group, Q, comprises:

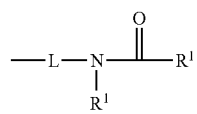
(Formula Id)

wherein:
L is a straight or branched hydrocarbylene group having between 1-10 carbon atoms; and
R¹ is hydrogen or a straight or branched hydrocarbylene group having from 1-20 carbon atoms, which may optionally include at least one substituent selected from the group consisting of halo, oxo, hydroxyl, alkoxy, amino, amido, cycloalkyl, heterocycloalkyl, aryl, aryloxy, and heteroaryl.

8. The method of claim 1, wherein said modification group, Q, comprises:

$$-L-R^2 \quad \text{(Formula II)}$$

wherein:
L is a straight or branched hydrocarbylene group having between 1-10 carbon atoms; and
R² is hydrogen, cyano, or an optionally substituted carbocycle, heterocycle, aryl or heteroaryl having between 5-10 atoms.

9. The method of claim 1, wherein said modification group, Q, comprises:

-L$^a$-A-L$^b$-B       (Formula III)

wherein:
L$^a$ and L$^b$ are each independently a bond or a straight or branched hydrocarbylene group having between 1-8 carbon atoms;
A is O, S, S(O), S(O)$_2$, Se, CR$^3$R$^4$, NR$^3$, C(O), C(S) or CNR$^3$;
B is C(O)R$^3$, C(S)R$^3$, C(O)NR$^3$R$^4$, OR$^3$ or SR$^3$; and
R$^3$ and R$^4$ are each independently hydrogen or straight or branched hydrocarbylene group having from 1-20 carbon atoms, which may optionally include at least one substituent selected from the group consisting of hydrogen, aryl, alkyl, halo, oxo, hydroxyl, alkoxy, amino, amido, cycloalkyl, heterocycloalkyl, aryl, aryloxy, and heteroaryl.

10. The method of claim 1, wherein said modification group, Q, comprises:

-L$^a$-D-L$^b$-E-L$^c$-F       (Formula IV)

wherein:
L$^a$, L$^b$ and L$^c$ are each independently selected from a bond or a straight or branched hydrocarbylene group having between 1-8 carbon atoms;
D is O, S, S(O), S(O)$_2$, CR$^5$R$^6$, and NR$^5$;
E is O, S, S(O), S(O)$_2$, CR$^5$R$^6$, and NR$^6$;
F is hydrogen, C(O)R$^7$, C(S)R$^7$, C(O)NR$^7$R$^8$, OR$^7$ and SR$^7$;
R$^5$ and R$^6$ can each independently be hydrogen, alkyl, aryl, halo, oxo, hydroxyl, alkoxy, aryloxy or amino, or R$^5$ and R$^6$ can cooperate to form a mono or bicyclic ring consisting 5-10 atoms and including D, R$^5$, R$^6$, E and L$^b$, provided that when R$^5$ and R$^6$ cooperate to form a ring, n is from 0-2; and
R$^7$ and R$^8$ are each independently selected from the group consisting of hydrogen, alkyl, aryl, halo, oxo, hydroxyl, alkoxy, aryloxy, amino, amido, optionally substituted cycloalkyl, optionally substituted heterocycloalkyl, optionally substituted aryl, optionally substituted aryloxy, and optionally substituted heteroaryl.

11. The method of claim 1, wherein said modification group, Q, comprises one or more chemical moieties selected from the group consisting of 4-oxo-1-hexyl, 4-oxo-1-pentyl, 5-oxo-1-hexyl, 6-oxo-1-heptyl, 1-methyl-4-oxo-pentyl, 4-methylthio-1-butyl, 5-methyl-4-oxo-hexyl, 1-ethyl-4-oxo-pentyl, N-(2-hydroxyethyl)phthalimido, 2-(N-acetyl-N-methyl)aminoethyl, 2-(N-formyl-N-methyl)aminoethyl, 2-methyl-5-oxo-hexyl, 1,1-dimethyl-4-oxo-pentyl, 4-oxo-1-octyl, 4-oxo-1-tetradecyl, 4-oxo-1-eicosamyl, and 3-(N-tertbutyl-carboxamido)-1-propyl.

12. The method according to claim 1, wherein said modification group dissociates during the initial denaturation step of said amplification.

13. The method of claim 1, wherein said modification group partially or entirely dissociates at a temperature between about 37° C.-95° C.

14. The method of claim 1, wherein said modified oligonucleotide primer comprises a phosphotriester internucleotide linkage.

15. The method of claim 1, wherein said modification group impairs hybridization of the oligonucleotide primer to a nucleic acid sequence.

16. The method of claim 1, wherein t$_{1/2}$ of dissociation of said modification group is between about 0.1-120 minutes at 95° C.

17. The method of claim 1, wherein the modification group dissociates between 50-95° C.

18. The method of claim 1, wherein said nucleic acid amplification comprises a hot start polymerase.

19. The method of claim 1 wherein said modified oligonucleotide primer is at least 90% chirally pure.

20. The method of claim 1, wherein said oligonucleotide primer comprises a detectable label.

21. The method of claim 1, wherein said amplifying comprises polymerase chain reaction (PCR).

22. The method of claim 21, wherein said PCR comprises multiplex PCR.

23. The method of claim 22, wherein a first target comprises amplifying using unmodified primers and a second target is amplified using modified primers.

24. The method of claim 22, wherein a first target comprises amplifying using one or more primers with a first modification group and a second target is amplified using one or more modified primers with a second modification group, wherein said first and second modification groups are different.

25. The method of claim 1, wherein said amplifying comprises reverse transcriptase (RT).

26. The method of claim 25, wherein said modification group dissociates at about 37-70° C.

27. The method of claim 25, wherein said modification group dissociates at 42° C.

28. The method of claim 1, wherein said amplifying comprises subsequent enzymatic reactions in a single tube.

29. The method of claim 28, wherein said subsequent enzymatic reactions comprise reverse transcriptase (RT) as a first enzymatic reaction and polymerase chain reaction (PCR) as a second enzymatic reaction.

30. The method of claim 29, wherein said RT reaction comprises amplifying with one or more unmodified primers and said PCR reaction comprises amplifying with one or more modified primers.

31. The method of claim 29, wherein said RT reaction comprises amplifying with one or more of a first modified primer and said PCR reaction comprises amplifying with one or more of a second modified primer.

32. The method of claim 31, wherein said one or more of a first modified primer comprises a modification group that dissociates at about 42° C., and wherein said one or more of a second modified primer comprises a modification group that dissociates at about 95° C.

33. The method of claim 1, wherein said modified oligonucleotide primer comprises a modification group at the 3' terminal internucleotide linkage.

34. The method of claim 33, wherein said modified oligonucleotide primer further comprises a modification groups at the n-1 position; wherein n is the 3' terminal internucleotide linkage.

* * * * *

UNITED STATES PATENT AND TRADEMARK OFFICE
CERTIFICATE OF CORRECTION

| | | |
|---|---|---|
| PATENT NO. | : 8,361,753 B2 | Page 1 of 1 |
| APPLICATION NO. | : 11/750237 | |
| DATED | : January 29, 2013 | |
| INVENTOR(S) | : Gerald Zon and Alexandre Lebedev | |

It is certified that error appears in the above-identified patent and that said Letters Patent is hereby corrected as shown below:

In the Specification:

At Column 1, please replace lines 14-18 with the following:

--STATEMENT AS TO RIGHTS TO INVENTIONS MADE UNDER FEDERALLY SPONSORED RESEARCH OR DEVELOPMENT

This invention was made with Government support under contract GM072177 awarded by the National Institute for General Medical Science, the National Institutes of Health. The Government has certain rights in this invention.--

Signed and Sealed this
Twenty-fourth Day of June, 2014

Michelle K. Lee
*Deputy Director of the United States Patent and Trademark Office*